United States Patent [19]

Sato et al.

[11] Patent Number: 5,162,196
[45] Date of Patent: Nov. 10, 1992

[54] COLOR COUPLER FOR PHOTOGRAPHY AND SILVER HALIDE PHOTOGRAPHIC MATERIAL COMPRISING THE SAME

[75] Inventors: Kozo Sato; Yasuhiro Shimada; Hideaki Naruse, all of Minami-ashigara, Japan

[73] Assignee: Fuji Photo Film Co., Ltd., Kanagawa, Japan

[21] Appl. No.: 615,797

[22] Filed: Nov. 20, 1990

[30] Foreign Application Priority Data

Nov. 20, 1989 [JP] Japan ................... 1-301552

[51] Int. Cl.$^5$ .................. G03C 7/32; G03C 7/38
[52] U.S. Cl. ................... 430/384; 430/376; 430/385; 430/543; 430/556; 430/557; 430/558
[58] Field of Search .......... 430/556, 557, 558, 558 A, 430/384, 385, 386, 387, 543, 376

[56] References Cited

U.S. PATENT DOCUMENTS

| | | | |
|---|---|---|---|
| 2,380,809 | 6/1945 | Verkinderen | 430/558 |
| 2,435,173 | 1/1948 | Bavley | 430/556 |
| 2,473,166 | 6/1949 | Merckx | 430/558 |
| 2,897,079 | 7/1959 | De Cat et al. | 430/386 |
| 3,502,468 | 3/1970 | Rogers | 430/558 A |
| 4,871,652 | 10/1989 | Normandin | 430/387 |
| 5,066,576 | 11/1991 | Ichijima et al. | 430/558 |

FOREIGN PATENT DOCUMENTS

| | | | |
|---|---|---|---|
| 929970 | 1/1948 | France | 430/558 |
| 60-226555 | 11/1985 | Japan . | |
| 61-103862 | 5/1986 | Japan . | |
| 61-281156 | 12/1986 | Japan . | |
| 577295 | 5/1946 | United Kingdom | 430/558 |

OTHER PUBLICATIONS

Mees and James, *The Theory of the Photographic Process* 3rd Edition, 1966, p. 387.
JP-A 226555/1985 partial translation.
JP-A 103862/1986 partial translation.
JP-A 281156/1986 partial translation.

*Primary Examiner*—Lee C. Wright
*Attorney, Agent, or Firm*—Birch, Stewart, Kolasch & Birch

[57] ABSTRACT

The present invention relates to a novel color coupler for photography and a silver halide color photographic material comprising the same, wherein the color coupler is one of the $\beta,\gamma$-unsaturated nitriles represented by formula (I). The invention provides for a color coupler, particularly a cyan coupler, which forms color images less in subsidiary absorption, good in color reproduction, and excellent in fastness, and a silver halide color photographic material having color images as described above. Further the color coupler can be synthesized from inexpensive raw material at a low cost

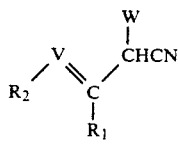

Formula (I)

wherein W represents a hydrogen atom or a group capable of being released when the compound is subjected to a coupling reaction with the oxidized product of an aromatic primary amine derivative, $R_1$ represents a represents a nitrogen atom, $R_2$ represents a substituent, if V represents

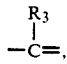

$R_2$ and $R_3$ each represent substituent, provided that at least one of $R_2$ and $R_3$ represents an electron attractive substituent, and provided that if $R_2$ or $R_3$ represents an aliphatic group or an aromatic group, the other does not represent an acyl group, and $R_1$ and $R_2$ may bond together to form a ring.

8 Claims, 1 Drawing Sheet

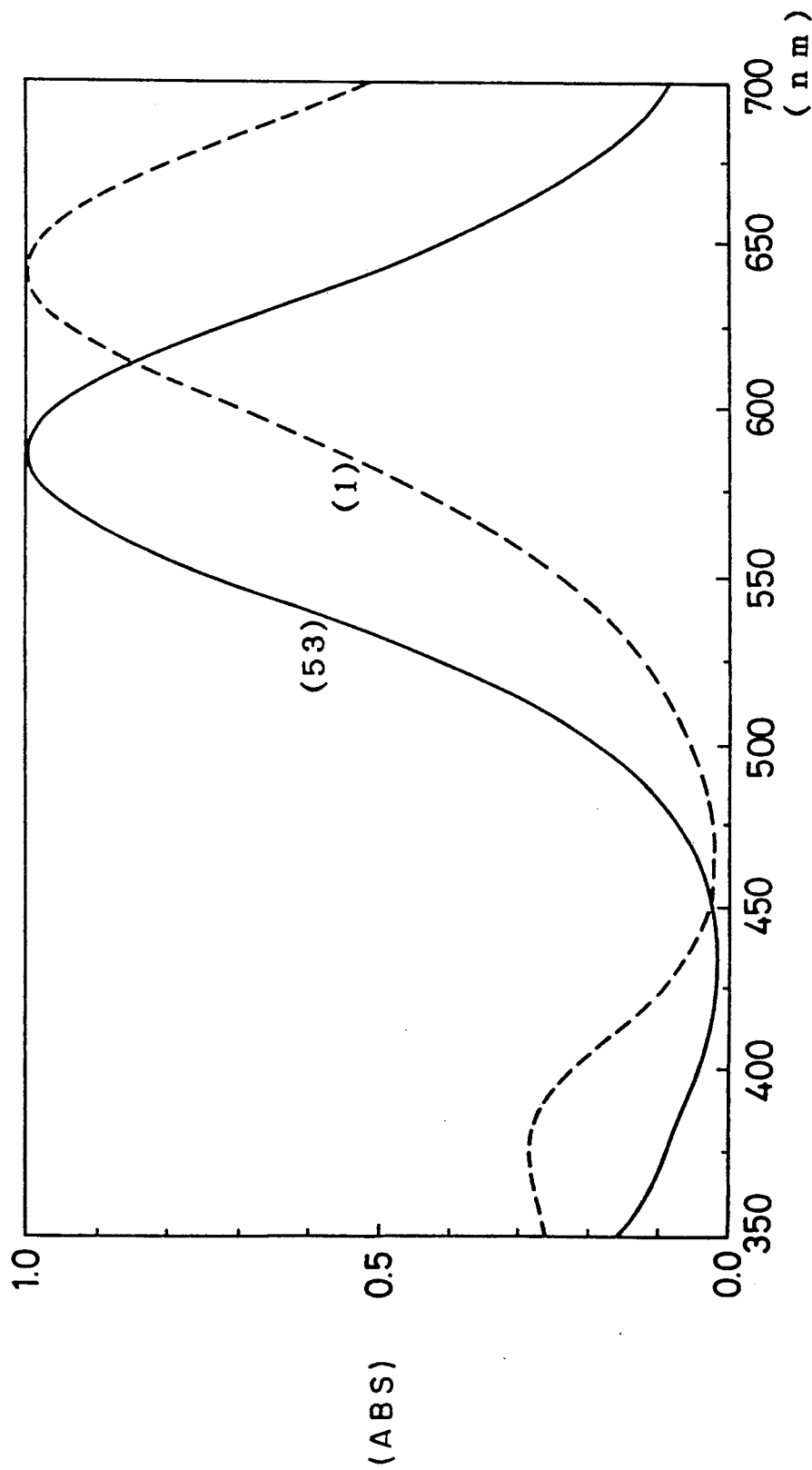

COLOR COUPLER FOR PHOTOGRAPHY AND SILVER HALIDE PHOTOGRAPHIC MATERIAL COMPRISING THE SAME

FIELD OF THE INVENTION

The present invention relates to a novel color coupler for photography, and to color photographic materials containing the same. More particularly, the present invention relates to silver halide color photographic materials improved in color reproduction owing to the use of novel cyan couplers.

BACKGROUND OF THE INVENTION

It is well known that an aromatic primary amine color-developing agent oxidized with an exposed silver halide that serves as an oxidizing agent can react with couplers to form dyes, such as indophenols, indoanilines, indamines, azomethines, phenoxazines, and phenazines, to form a color image. In such a photographic system, the subtractive color process is used to form a color image consisting of a yellow dye, a magenta dye, and a cyan dye.

Of these, a phenol coupler or a naphthol coupler is generally used to form a cyan color image. However, since these couplers have undesired absorption in the green region, they have the serious problem that color reproduction is extremely deteriorated.

As means of solving the problem, various compounds have been proposed, but at present, there are no compounds that exhibit a satisfactory performance.

SUMMARY OF THE INVENTION

Therefore, the first object of the present invention is to provide a novel coupler capable of forming a dye having less subsidiary absorption and having a high molar absorptivity coefficient, and in particular a color photographic material containing such a cyan coupler.

The second object of the present invention is to provide a novel coupler excellent in coupling activity, a method for forming a color image using the same, and a color photographic material containing the same.

The third object of the present invention is to provide a coupler that can be prepared in a synthesis having a small number of steps, which is advantageous in view of cost, and a color photographic material containing the same.

The fourth object of the present invention is to provide a color photographic material that can give a cyan image excellent in image fastness.

Other and further objects, features, and advantages of the invention will be appear more fully from the following description taken in connection with the accompanying drawing.

BRIEF DESCRIPTION OF THE DRAWING

FIG. 1 is a diagram of the absorption spectra of dyes, wherein the absorbance is plotted along the ordinate and the absorption wavelength (nm) is plotted along the abscissa.

DETAILED DESCRIPTION OF THE INVENTION

The objects of the present invention have been achieved by providing color couplers for photography represented by the following formula (I), a method for forming a color image using the same, and silver halide color photographic materials containing them.

Formula (I)

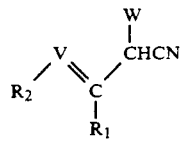

wherein W represents a hydrogen atom or a group capable of being released when the compound is subjected to a coupling reaction with the oxidized product of an aromatic primary amine derivative, $R_1$ represents a substituent, V represents a nitrogen atom or

if V represents a nitrogen atom, $R_2$ represents a substituent, if V represents

$R_2$ and $R_3$ each represent substituent, provided that at least one of $R_2$ and $R_3$ represents an electron attractive substituent, and provided that if $R_2$ or $R_3$ represents an aliphatic group or an aromatic group, the other does not represent an acyl group, and $R_1$ and $R_2$ may bond together to form a ring.

Compounds of the present invention will now be further described in more detail.

In formula (I), $R_1$ represents a substituent, and as substituent can be mentioned, for example, a halogen atom, an aliphatic group preferably having 1 to 36 carbon atoms, an aromatic group preferably having 3 to 36 carbon atoms (e.g., phenyl, naphthyl, and 2,4-dichlorophenyl), a heterocyclic group preferably having 1 to 12 carbon atoms (e.g., 3-pyridyl and 2-furyl), an alkoxy group preferably having 1 to 20 carbon atoms (e.g., methoxy and 2-methoxyethoxy), an aryloxy group preferably having 6 to 36 carbon atoms (e.g., 2,4-di-tert-amylphenoxy, 2-chlorophenoxy, and 4-cyanophenoxy), an alkenyloxy group preferably having 1 to 20 carbon atoms (e.g., 2-propenyloxy), an amino group preferably having 1 to 20 carbon atoms (e.g., butylamino, dimethylamino, anilino, and N-methylanilino), an acyl group preferably having 1 to 20 carbon atoms (e.g., acetyl and benzoyl), an ester group preferably having 1 to 20 carbon atoms (e.g., butoxycarbonyl, phenoxycarbonyl, acetoxy, benzoyloxy, butoxysulfonyl, and toluenesulfonyloxy), an amido group preferably having 1 to 20 carbon atoms (e.g., acetylamino, ethylcarbamoyl, dimethylcarbamoyl, methanesulfonamido, and butylsulfamoyl), a sulfamido group preferably having 1 to 20 carbon atoms (e.g., dipropylsulfamoylamino), an imido group preferably having 4 to 20 carbon atoms (e.g., succinimido and hidantoinyl), a ureido group preferably having 1 to 20 carbon atoms (e.g., phenylureido and dimethylureido), an aliphatic or aromatic sulfonyl group preferably having 1 to 20 carbon atoms (e.g., methanesulfonyl and phenylsulfonyl), an aliphatic or aromatic thio group preferably having 1 to 20 carbon atoms (e.g., ethylthio and phenylthio), a hydroxy group, a cyano group, a carboxy group, a nitro group, and a sulfo group.

In this specification and claims the term "aliphatic group" means a straight-chain, branched, or cyclic aliphatic hydrocarbon group, including saturated and unsaturated ones, such as alkyl groups, alkenyl groups, and alkynyl groups. Typical examples thereof include a methyl group, an ethyl group, a butyl group, a dodecyl group, an octadecyl group, an eicosenyl group, an isopropyl group, a tert-butyl group, a tert-octyl group, a tert-dodecyl group, a cyclohexyl group, a cyclopentyl group, an ally group, a vinyl group, a 2-hexadecenyl group, and a propargyl group.

In formula (I), if V represents

at least one of $R_2$ and $R_3$ represents an electron attractive substituent, preferably a substituent or an atom wherein the value of the Hammett substituent constant $\sigma_p$ is 0.10 or over, preferably 0.35 or over, and more preferably 0.60 or over. It is preferable that the value of the $\sigma_p$ is 2 or below. As the value of the Hammett substituent constant $\sigma_p$ used herein, the value reported by Hansch, C. Leo et al. [e.g., in J. Med. Chem. 16, 1207 (1973); and ibid. 20, 304 (1977)] is preferably used.

A substituent or atom wherein the value of the $\sigma_p$ is 0.10 or over includes a chlorine atom, a bromine atom, an iodine atom, a substituted alkyl group (e.g., trichloromethyl, trifluoromethyl, chloromethyl, trifluoromethylthiomethyl, trifluoromethanesulfonylmethyl, and perfluorobutyl), a nitrile group, an acyl group (e.g., formyl, acetyl, and benzoyl), a carboxyl group, a substituted or unsubstituted carbamoyl group (e.g., carbamoyl and methylcarbamoyl), an alkoxycarbonyl (e.g., methoxycarbonyl, ethoxycarbonyl, and diphenylmethylcarbonyl), an aromatic group substituted by another electron attractive group (e.g., pentachlorophenyl and pentafluorophenyl), a heterocyclic residue (e.g., 2-benzooxazolyl, 2-benzthiazolyl, 1-phenyl-2-benzimidazolyl, and 1tetrazolyl), a nitro group, an azo group (e.g., phenylazo), an amino group substituted by another electron attractive group (e.g., ditrifluoromethylamino), an alkoxy group substituted by another electron attractive group (e.g., trifluoromethoxy), an alkylsulfonyloxy group (e.g., methanesulfonyloxy), an acyloxy group (e.g., acetyloxy and benzoyloxy), an arylsulfonyloxy group (e.g., benzenesulfonyloxy), a phosphoryl group (e.g., dimethoxyphosphoryl and diphenylphosphoryl), a sulfamoyl group, and a sulfonyl group (e.g., trifluoromethanesulfonyl, methanesulfonyl, and benzenesulfonyl).

A substituent wherein the value of the $\sigma_p$ is 0.35 or over includes an alkyl substituted by another electron attractive group (e.g., trifluoromethyl and perfluorobutyl), a nitrile group, an acyl group (e.g., acetyl, benzoyl, and formyl), a carboxyl group, a carbamoyl group (e.g., carbamoyl and methylcarbamoyl), an alkoxycarbonyl group (e.g., methoxycarbonyl, ethoxycarbonyl, and diphenylmethylcarbonyl), an aromatic group substituted by another electron attractive group (e.g., pentafluorophenyl), a nitro group, an azo group (e.g., 1-tetrazolyl), a nitro group, an azo group (e.g., phenylazo), an amino group substituted by another electron attractive group (e.g., ditrifluoromethylamino), an alkoxy group substituted by another electron attractive group (e.g., trifluoromethoxy), an alkylsulfonyloxy group (e.g., methanesulfonyloxy), a phosphoryl group (e.g., dimethoxyphosphoryl and diphenylphosphoryl), a sulfamoyl group, and a sulfonyl group (e.g., trifluoromethanesulfonyl, methanesulfonyl, and benzenesulfonyl).

A substituent wherein the value of the $\sigma_p$ is 0.60 or over includes a nitrile group, a nitro group, and a sulfonyl group (e.g., trifluoromethanesulfonyl, difluoromethanesulfonyl, methanesulfonyl, and benzenesulfonyl).

When $R_2$ or $R_3$ is not an electron attractive group, the substituent represents, for example, an aliphatic group (e.g., methyl, ethyl, or octyl), an alkoxy group (e.g., methoxy, ethoxy, and dodecyloxy), an amido group (e.g., acetamido, pivalylamido, and octaneamido), an aromatic group that is not substituted by an electron attractive group (e.g., phenyl and 4-alkoxyphenyl), and a heterocyclic group (e.g., 2-furyl, 2-thienyl, and 2 -thiazolyl), provided that if one of $R_2$ and $R_3$ represents said aliphatic group or said aromatic group, the other is not an acyl group.

In the present invention, of compounds represented by formula (I), compounds represented by the following formula (II) or (III) are preferable.

Formula (II)

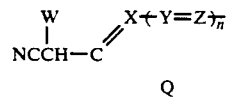

wherein W has the same meaning as in formula (I) X, Y, and Z each represent a nitrogen atom, a methine group, or a methine group having an electron attractive group, with at least one of X, Y, and Z being a methine group having an electron-attractive group, n is 1 or 2, and Q represents a group of nonmetal atoms required to form a heterocyclic ring or an aromatic ring together with the

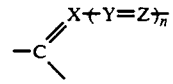

residue.

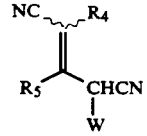

Formula (III)

wherein W has the same meaning as in formula (I), and $R_4$ and $R_5$ each represent a substituent, provided that at least one of $R_4$ and $R_5$ represents an electron attractive substituent, and provided that $R_4$ and $R_5$ does not bond to form a ring. In the present invention compounds represented by formula (III) are most preferable.

In formula (II), X, Y, and Z each represent a nitrogen atom, a methine group, or a methine group having an electron attractive group, at least one of them represents a methine group having an electron attractive group, and if X represents a methine group as defined above, it is

if Y represents a methine group as defined above, it is

and if Z represents a methine group as defined above, it is

If X and Y each represent a methine group as defined above, $R_6$ and $R_7$ may be the same or different, and they may bond together to form a ring. Similarly, if Y and Z each represent a methine group as defined above, $R_7$ and $R_8$ may be the same or different, and they may bond together to form a ring. In that case, preferably it forms a condensed ring such as a benzene condensed ring or a pyridine condensed ring.

$R_6$, $R_7$ and $R_8$ each represent an electron attractive substituent and, preferably, a substituent wherein the value of the Hammett substituent constant $\sigma_p$ is 0.10 or over, more preferably 0.35 or over, and further more preferably 0.60 or over. As the substituents, those substituents listed for $R_2$ or $R_3$ can be mentioned.

In formula (II), Q represents an atom or an atomic group required to form together with the bonded carbon atoms or nitrogen atom a ring having 5 or more members, preferably 5 to 8 members, and more preferably 5 to 6 members, and the bivalent group that forms the ring includes a bivalent amino group, an ether linkage, a thioether linkage, an alkylene group, an alkenylene group, an imino group, a sulfonyl group, and a carbonyl group, which may have a substituent. As the substituent, those listed for $R_1$ can be mentioned.

Particularly preferably, Q represents a thioether linkage, an imino group, or a sulfonyl group.

In formula (III), at least one of $R_4$ and $R_5$ represents an electron attractive substituent and, preferably, a substituent wherein the value of the Hammett substituent constant $\sigma_p$ is 0.10 or over, more preferably 0.35 or over, and further more preferably 0.60 or over. The substituent includes those substituents listed for $R_2$ or $R_3$.

If $R_4$ or $R_5$ represents a substituent, the substituent includes, for example, an aliphatic group preferably having 1 to 36 carbon atoms (e.g., methyl, propyl, t-butyl, tridecyl, 3-(2,4-di-t-amylphenoxy)propyl, 2-dodecyloxyethyl, 3-phenoxypropyl, cyclopentyl, benzyl, allyl, and propargyl), an aromatic group preferably having 6 to 36 carbon atoms (e.g., phenyl and naphthyl), and a heterocyclic group (e.g., 2-furyl, 2-thienyl, 2-pyrimidyl, and 2-thiazolyl). $R_4$ and $R_5$ may bond at cis-position or at trans-position.

In formulae (I), (II), and (III), W represents a hydrogen atom or a group capable of being released that will release when the coupler is subjected to a coupling reaction with the oxidized product of an aromatic primary amine derivative (hereinafter referred to as "group capable of being released") and when W represents a group capable of being released, the group capable of being released is a halogen atom, an aromatic azo group, a group that bonds through an oxygen, nitrogen, sulfur, or carbon atom to an aliphatic group, an aromatic group, a heterocyclic group, an aliphatic, aromatic, or heterocyclic sulfonyl group, or an aliphatic, aromatic, or heterocyclic carbonyl group, or a heterocyclic group that bonds to the coupling site through a nitrogen atom, and the aliphatic group, the aromatic group, or the heterocyclic group contained in the group capable of being released may be substituted by one or more substituents acceptable to $R_1$, which substituents may be the same or different and may be further substituted by a substituent acceptable to $R_1$.

The group capable of being released is a group that is capable of being released when the coupler reacts with the oxidized product of a developing agent and specific examples thereof include a halogen atom (e.g., fluorine, chlorine, and bromine), an alkoxy group (e.g., ethoxy, dodecyloxy, methoxyethylcarbamoylmethoxy, carboxypropyloxy, and methanesulfonylethoxy), an aryloxy group (e.g., 4-chlorophenoxy, 4-methoxyphenoxy, and 4-carboxyphenoxy), an acyloxy group (e.g., acetoxy, tetradecanoyloxy, and benzoyloxy), an aliphatic or aromatic sulfonyloxy group (e.g., methanesulfonyloxy and toluenesulfonyloxy), an acylamino group (e.g., dichloroacetylamino and heptafluorobutyrylamino), an aliphatic or aromatic sulfonamido group (e.g., methanesulfonamido and p-toluenesulfonamido), an alkoxycarbonyloxy group (e.g., ethoxycarbonyloxy and benzyloxycarbonyloxy), an aryloxycarbonyloxy group (e.g., phenoxycarbonyloxy), an aliphatic, aromatic, or heterocyclic thio group (e.g., ethylthio, 2-carboxyethylthio, phenylthio, and tetrazolylthio), a carbamoylamino group (e.g., N-methylcarbamoylamino and N-phenylcarbamoylamino), a 5- or 6-membered nitrogen-containing heterocyclic group (e.g., imidazolyl, pyrazolyl, triazolyl, tetrazolyl, and 1,2-dihydro-2-oxo-1-pyridyl), an imido group (e.g., succinimido and hydantoinyl), and an aromatic azo group (e.g., phenylazo), which may be further substituted by substituents acceptable to $R_1$. As the group capable of being released bonded through the carbon atom, bis-type couplers obtained by condensing a 4-equivalent coupler with aldehydes or ketones can be mentioned. The group capable of being released upon the coupling reaction of the present invention may contain a photographically useful group as a development inhibitor or development accelerator.

The compounds of the present invention are useful as photographic couplers, and particularly as cyan couplers.

The compound of the present invention represented by formula (I) is one of the $\beta,\gamma$-unsaturated nitriles, and specific examples of the compounds of the present invention are shown below, but the present invention is not limited to them.

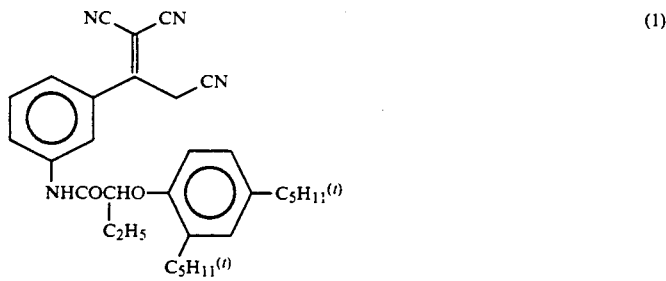 (1)
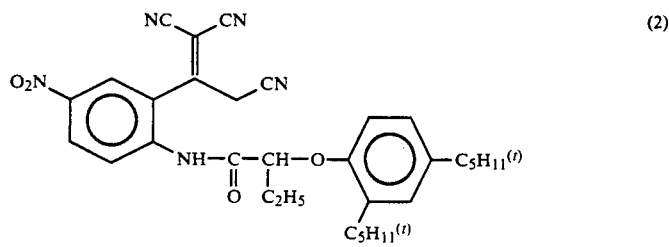 (2)
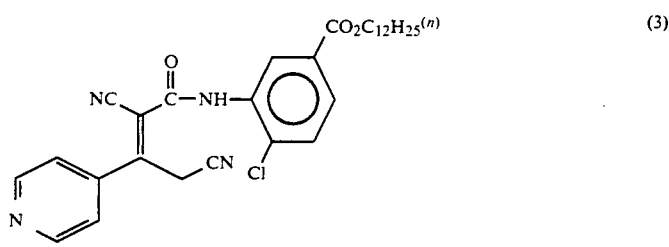 (3)
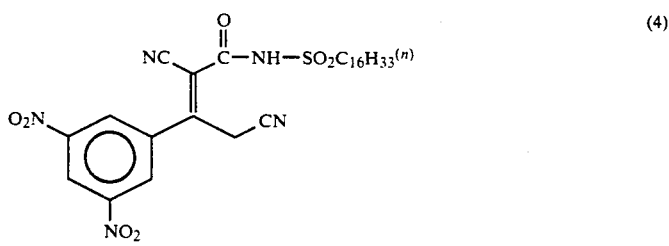 (4)
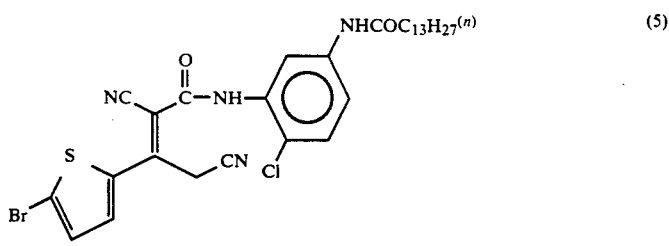 (5)
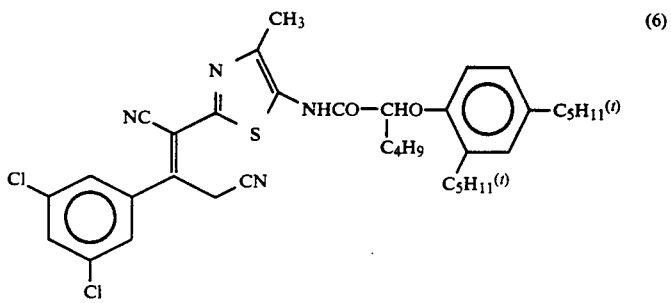 (6)

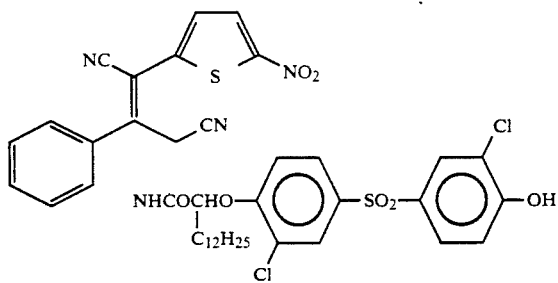
(7)
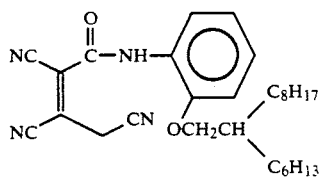
(8)
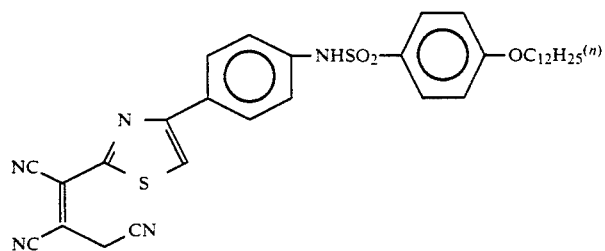
(9)
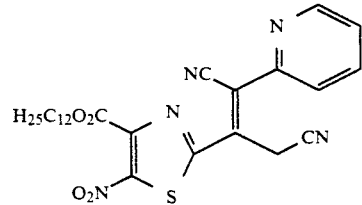
(10)
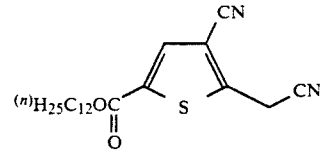
(11)
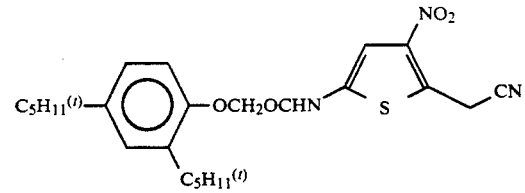
(12)
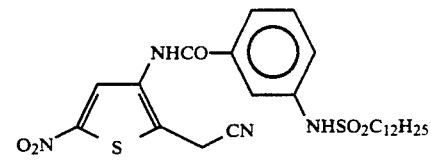
(13)
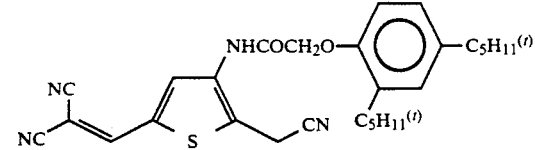
(14)

-continued
(15)
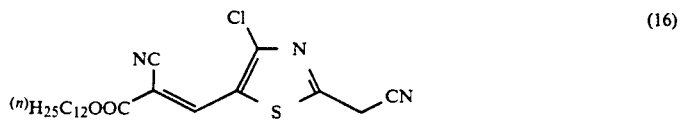
(16)
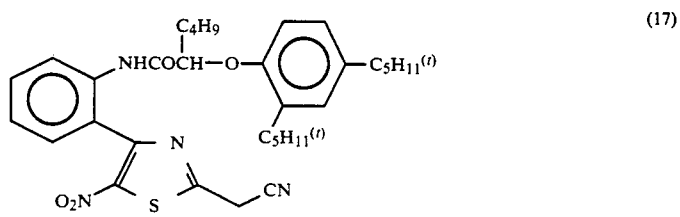
(17)
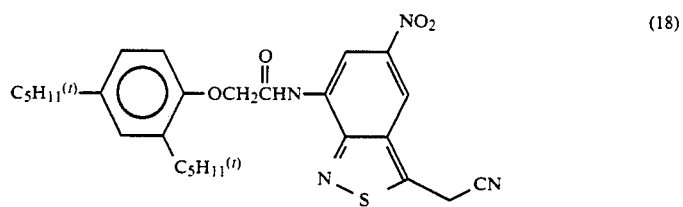
(18)
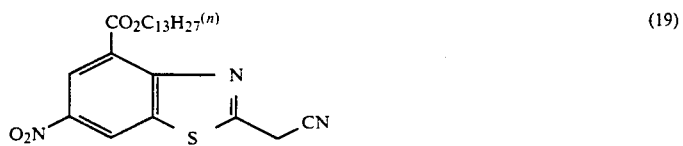
(19)
(20)
(21)
(22)
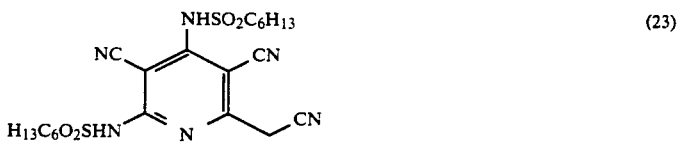
(23)

-continued
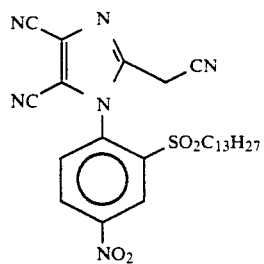
(24)
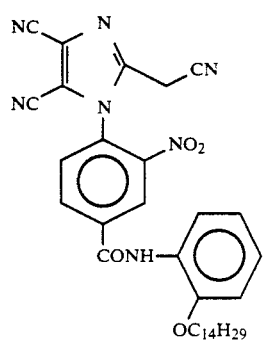
(25)
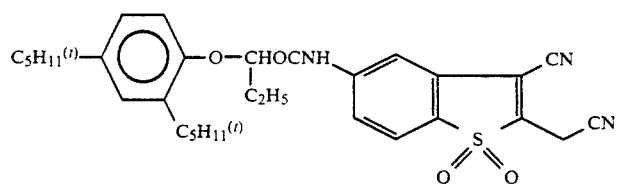
(26)
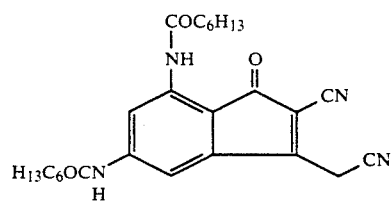
(27)
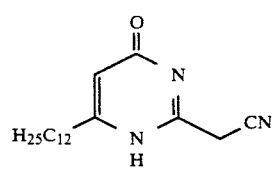
(28)
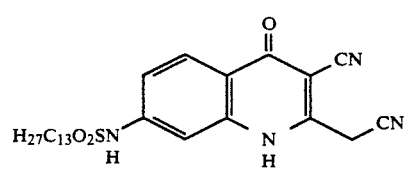
(29)
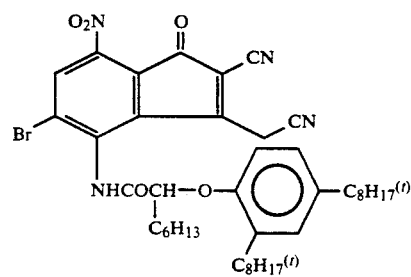
(30)

-continued
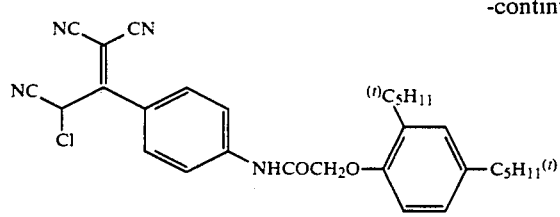 (31)
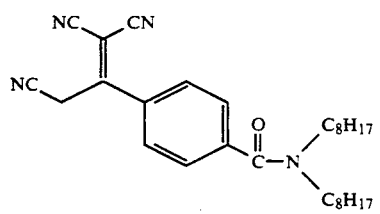 (32)
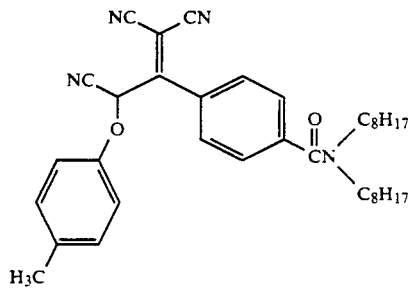 (33)
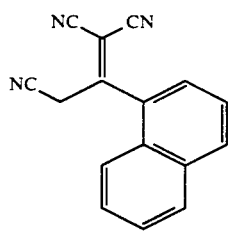 (34)
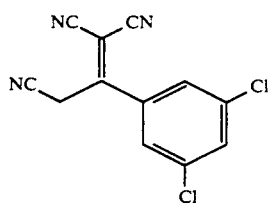 (35)
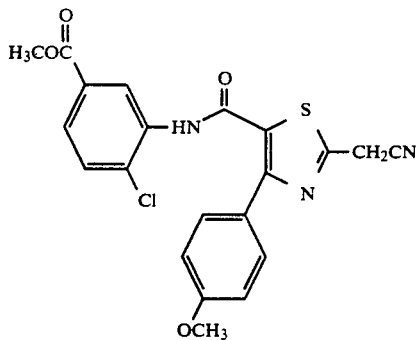 (36)
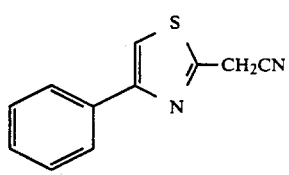 (37)

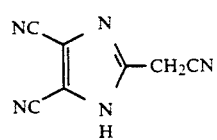
(38)
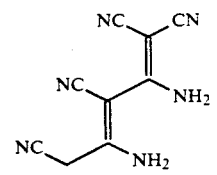
(39)
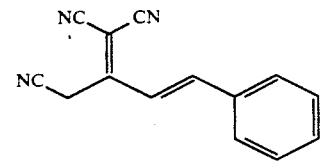
(40)
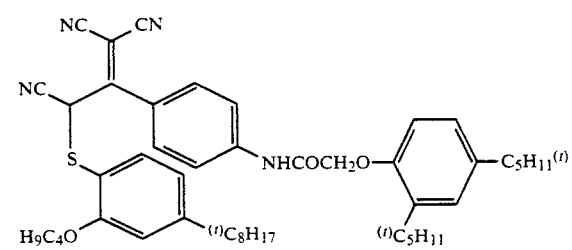
(41)
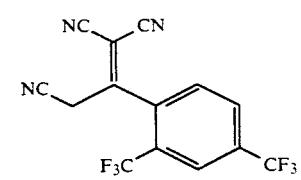
(42)
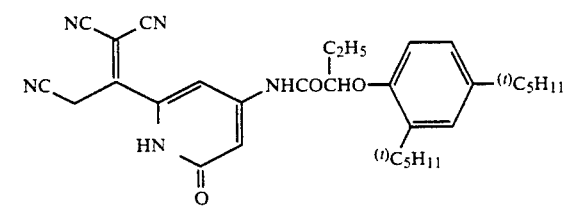
(43)
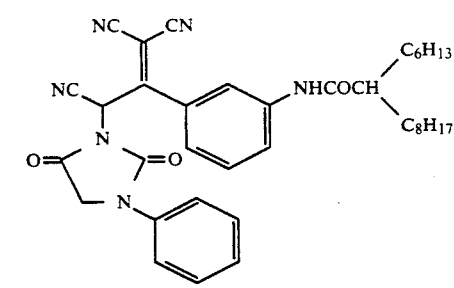
(44)
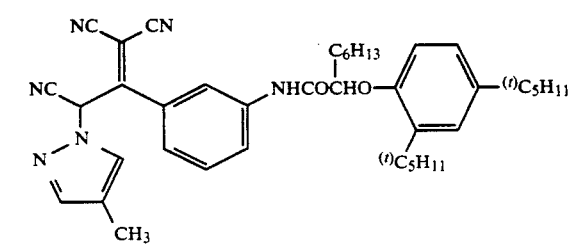
(45)

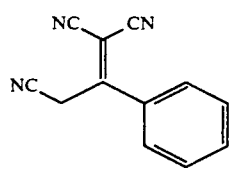

(46)

Next, synthesis examples are described below.

SYNTHESIS EXAMPLE 1

Synthesis of Exemplified Compound (1)

Exemplified compound (1) was synthesized according to the following route:

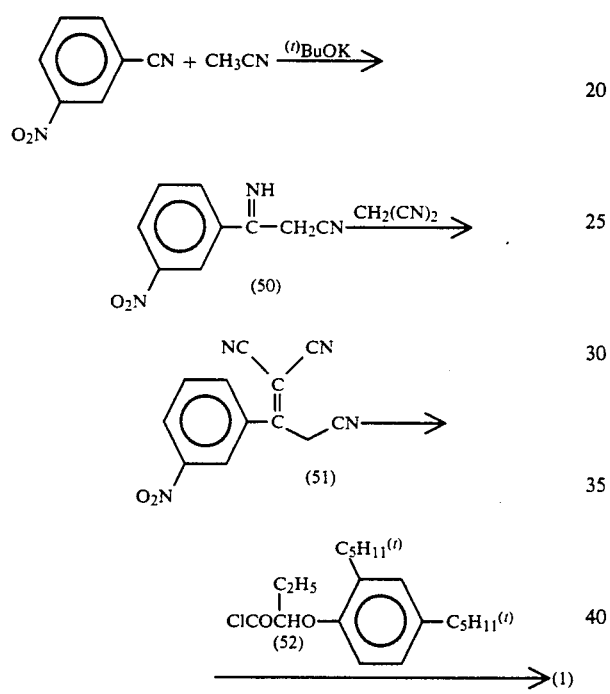

Synthesis of Intermediate Product (50)

7.4 g of 3-nitrobenzonitrile and 10.5 ml of acetonitrile were dissolved in 30 ml of anhydrous tetrahydrofuran, then 5.6 g of potassium t-butoxide was added slowly at room temperature, and after the reaction solution turned dark brown it was heated under reflux. After the reaction 100 ml of ethyl acetate and 100 ml of water were added, and then hydrochloric acid was added to neutralize it, followed by washing with water. The ethyl acetate layer was dried over magnesium sulfate, then the ethyl acetate was distilled off under reduced pressure and the residue was purified by column chromatography, to obtain 9.45 g of intermediate product (50).

Synthesis of Exemplified Compound (1)

2.4 g of intermediate product (50) and 1.2 g of malononitrile were dissolved in 10 ml of ethanol and the solution was heated under reflux for 3 hours. After the reaction hydrochloric acid was added and the precipitated crystals were filtered in order to obtain 3.2 g of Intermediate Product (51). The resulting intermediate product (51) was reduced with iron in the usual manner, to obtain the desired exemplified compound (1).

The result of elementary analysis of exemplified compound (1) is shown in the following Table A.

TABLE A

| | H (%) | C (%) | N (%) |
|---|---|---|---|
| Calculated | 7.50 | 75.26 | 10.97 |
| Found | 7.45 | 74.98 | 10.85 |

SYNTHESIS EXAMPLE 2

Synthesis of Exemplified Compound (32)

Exemplified compound (32) was synthesized according to the following route:

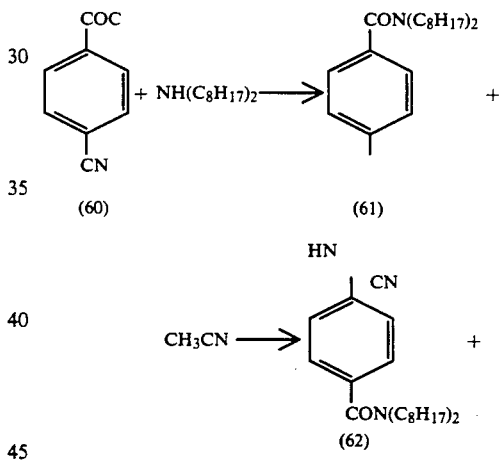

NCCH₂CN ⟶ Exemplified compound (32)

Synthesis of Intermediate Product (62)

72.0 g of dioctylamine and 40.4 g of triethylamine were dissolved in 300 ml of tetrahydrofuran, and then p-cyanobenzoylchloride (60) was added slowly while maintaining the reaction temperature at 10° to 15° C. After the reaction 300 ml of ethyl acetate was added and the solution was washed with water. After drying ethyl acetate was distilled off to obtain 96.5 g of intermediate product (61). Then, 95.7 g of intermediate product (61) dissolved in 120 ml of acetonitrile was added dropwisely to 450 ml solution of tetrahydrofuran containing 20.8 g of 60% hydrogenated sodium under reflux. After the reaction, the solution was neutralized by hydrochloric acid solution and ethyl acetate and water were added to the solution, followed by extraction. The ethyl acetate layer was dried and distilled off to obtain 106.3 g of intermediate product (62).

Synthesis of Exemplified Compound (32)

106.3 g of intermediate product (62) and 19.8 g of malononitrile were dissolved in 200 ml of ethanol, and the solution was heated under reflux for 3 hours. After the reaction ethanol was distilled off, and to the residue 200 ml of ethyl acetate and 200 ml of water were added, followed by extraction. The ethyl acetate layer was dried and ethyl acetate was distilled off, and then the residue was separated by column chromatography to obtain 110.4 g of desired exemplified compound (32). m.p.: 189°–190° C.

SYNTHESIS EXAMPLE 3

Synthesis of Exemplified Compound (38)

Exemplified compound (38) was synthesized according to the following route:

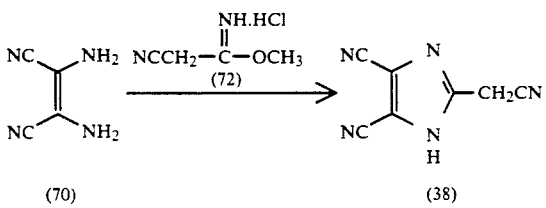

21.6 Grams of compound (70) and 26.9 g of compound (71) were dissolved in 300 ml of ethanol and the solution was stirred to proceed reaction for 2 hours at room temperature and then for 2 hours at 40° to 50° C. After the reaction 500 ml of ethyl acetate was added to the solution and the mixture was thoroughly washed with water. The ethyl acetate layer was dried and distilled off under reduced pressure to attain 26.7 g of the desired exemplified compound (38) m.p.: 160° C.

In a similar manner, Exemplified Compounds (2) to (4) and (6) to (10) were synthesized.

Exemplified Compounds (21) and (23) can be synthesized with reference being made, for example, to Journal f. Prabt. Band 316, Heft 4, 684 (1974), JP-A ("JP-A" means unexamined published Japanese patent application) Nos. 77366/1975 and 77365/1075, and Aust. J. Chem. 26 2567 (1973).

The compound of the present invention can be synthesized as described above. In that case, a group capable of being released upon coupling reaction that is represented by W in formula (I) can be introduced by, for example, such a method as described below:

(1) halogen atom: method of halogenating the coupling position of a 4-equivalent coupler;

(2) a group bonded through oxygen atom: method of halogenating the coupling position of a 4-equivalent coupler and then reacting with phenol compound in the presence of a base;

(3) a group bonded through sulfur atom: method of reacting a 4-equivalent coupler with sulfenyl chloride that is to be released, in the presence of a base or without a base;

(4) a group bonded though nitrogen atom: method of introducing a nitroso group in the coupling position of 4-equivalent coupler with an adequate agent for introducing a nitroso group and then reducing by a suitable procedure (e.g., hydrogenation catalized by Pd-C catalizer or the like or chemical reduction using stannous chloride or the like), followed by reaction with various halide.

These methods introducing a group capable of being released are known per se, and can be referred to, for example in U.S. Pat. Nos. 3,894,875, 3,933,501, 4,296,199, 3,227,554, 3,476,563, and 4,296,200.

The compound of the present invention represented by formula (I) forms a dye by a coupling reaction with the oxidized product of an aromatic primary amine developing-agent. The dye can be utilized as a cyan dye in various usages (e.g., filter, paint, ink, dye for recording image or information or dye for printing).

The color coupler of the present invention is preferably contained in a photosensitive silver halide emulsion layer, particularly in a red-sensitive silver halide emulsion layer.

The standard amount of the color coupler of the present invention to be used is 0.002 to 1 mol, preferably 0.1 to 0.5 mol, per mol of a photosensitive silver halide.

Further, when the coupler of the present invention is soluble in an aqueous alkali solution, it can be used for forming a color dye in so-called coupler-in-developer-type development where the coupler is dissolved together with developing-agent and other additives in an aqueous alkali solution. The amount of the coupler to be added in such case is 0.0005 to 0.05 mol, preferably 0.005 to 0.002 mol, per liter of color-developer.

The coupler of the present invention can be introduced into a photographic material by various known dispersion processes, such as the solid dispersion process and the alkali dispersion process, preferably the latex dispersion process, and more preferably the oil-in-water dispersion process, which is a typical example. In the oil-in-water dispersion process, the coupler of the present invention will be dissolved in a high-boiling organic solvent, having a boiling point of 175° C. or over, and/or a low-boiling so-called co-solvent, and the solution will be finely dispersed in water or an aqueous medium, such as an aqueous gelatin solution, in the presence of a surface-active agent. The dispersion may be accompanied by phase inversion, and if necessary, after the co-solvent is removed or reduced for example by distillation, noodle washing, or ultrafiltration, it may be used for application.

The coupler of the present invention can be applied to negative-working photographic materials or positive-working photographic materials, or to photographic materials which will be subjected to wet-development processing, or to photographic materials which will be subjected to dry-development processing such as thermal-development processing.

Specifically, the coupler of the present invention can be applied, for example, to color negative films, reversal color films, color papers (for print), direct positive photographic materials, reversal color papers, thermal color development photographic materials, and color diffusion transfer photographic materials. As the silver halide used in such photographic materials, silver chloride, silver bromide, silver bromoiodide, and silver chlorobromide can be exemplified.

Typical additives and materials suitable to be used for color papers will be described below, which will also be applied to other photographic materials.

The color photographic material of the present invention can be constituted by applying at least each of a blue-sensitive silver halide emulsion layer, a green-sensitive silver halide emulsion layer, and a red-sensitive silver halide emulsion layer on a base. For common color print papers, the above silver halide emulsion layers are applied in the above-stated order on the base, but the order may be changed. Color reproduction by the subtractive color process can be performed by incorporating, into these photosensitive emulsion layers, silver halide emulsions sensitive to respective wavelength ranges, and so-called colored-couplers capable of forming dyes complementary to light to which the couplers are respectively sensitive, that is, capable of forming yellow dye complementary to blue light, magenta dye complementary to green light, and cyan dye complementary to red light. However, the constitution may be such that the photosensitive layers and the color formed from the couplers do not have the above relationship.

As the silver halide emulsion used in the present invention, one comprising silver chlorobromide or silver chloride and being substantially free from silver iodide can be preferably used. Herein the term "substantially free from silver iodide" means that the silver iodide content is 1 mol % or below, and preferably 0.2 mol % or below. Although the halogen compositions of the emulsions may be the same or different from grain to grain, if emulsions whose grains have the same halogen composition are used, it is easy to make the properties of the grains homogeneous. With respect to the halogen composition distribution in a silver halide emulsion grain, for example, a grain having a so-called uniform-type structure, wherein the composition is uniform throughout the silver halide grain, a grain having a so-called layered-type structure, wherein the halogen composition of the core of the silver halide grain is different from that of the shell (which may comprise a single layer or layers) surrounding the core, or a grain having a structure with nonlayered parts different in halogen composition in the grain or on the surface of the grain (if the nonlayered parts are present on the surface of the grain, the structure has parts different in halogen composition joined onto the edges, the corners, or the planes of the grain) may be suitably selected and used. To secure high sensitivity, it is more advantageous to use either of the latter two than to use grains having a uniform-type structure, which is also preferable in view of the pressure resistance. If the silver halide grains have the above-mentioned structure, the boundary section between parts different in halogen composition may be a clear boundary, or an unclear boundary, due to the formation of mixed crystals caused by the difference in composition, or it may have positively varied continuous structures.

As to the silver halide composition of these silver chlorobromide emulsions, the ratio of silver bromide/silver chloride can be selected arbitrarily. That is, the ratio is selected from the broad range in accordance with the purpose, but the ratio of silver chloride in a silver chlorobromide is preferably 2% or over.

Further in the photographic material suitable for a rapid processing an emulsion of high silver chloride content, so-called a high-silver-chloride emulsion may be used preferably. The content of silver chloride of the high-silver-chloride emulsion is preferably 90 mol % or over, more preferably 95 mol % or over.

In these high-silver-chloride emulsions, the structure is preferably such that the silver bromide localized phase in the layered form or nonlayered form is present in the silver halide grain and/or on the surface of the silver halide grain as mentioned above. The silver bromide content of the composition of the above-mentioned localized phase is preferably at least 10 mol %, and more preferably over 20 mol %. The localized phase may be present in the grain, or on the edges, or corners of the grain surfaces, or on the planes of the grains, and a preferable example is a localized layer epitaxially grown on each corner of the grain.

On the other hand, for the purpose of suppressing the lowering of the sensitivity as much as possible when the photographic material undergoes pressure, even in the case of high-silver-chloride emulsions having a silver chloride content of 90 mol % or over, it is preferably also practiced to use grains having a uniform-type structure, wherein the distribution of the halogen composition in the grain is small.

In order to reduce the replenishing amount of the development processing solution, it is also effective to increase the silver chloride content of the silver halide emulsion. In such a case, an emulsion whose silver chloride is almost pure, that is, whose silver chloride content is 98 to 100 mol %, is also preferably used.

The average grain size of the silver halide grains contained in the silver halide emulsion used in the present invention (the diameter of a circle equivalent to the projected area of the grain is assumed to be the grain size, and the number average of grain sizes is assumed to be an average grain size) is preferably 0.1 to 2 μm.

Further, the grain size distribution thereof is preferably one that is a so-called monodisperse dispersion, having a deviation coefficient (obtained by dividing the standard deviation of the grain size by the average grain size) of 20% or below, and desirably 15% or below. In this case, for the purpose of obtaining one having a wide latitude, it is also preferable that monodisperse emulsions as mentioned above are blended to be used in the same layer, or are applied in layers.

As to the shape of the silver halide grains contained in the photographic emulsion, use can be made of grain in a regular crystal form, such as cubic, tetradecahedral, or octahedral, or grains in an irregular crystal form, such as spherical or planar, or grains that are a composite of these. Also, a mixture of silver halide grains having various crystal forms can be used. In the present invention, of these, grains containing grains in a regular crystal form in an amount of 50% or over, preferably 70% or over, and more preferably 90% or over, are preferred.

Further, besides those mentioned above, an emulsion wherein the tabular grains having an average aspect ratio (the diameter of a circle calculated/the thickness) of 5 or over, and preferably 8 or over, exceed 50% of the total of the grains in terms of the projected area, can be preferably used.

The silver chloromide emulsion used in the present invention can be prepared by methods described, for example, by P. Glafkides, in *Chimie et Phisicue Photoraphique* (published by Paul Montel, 1967), by G. F. Duffin in *Photographic Emulsion Chemistry* (published by Focal Press, 1966), and by V. L. Zelikman et al. in *Making and Coating Photographic Emulsion* (published by Focal Press, 1964). That is, any of the acid process, the neutral process, the ammonia process, etc. can be used, and to react a soluble silver salt and a soluble halide, for example, any of the single-jet process, the double-jet process, or a combination of these can be used. A process of forming grains in an atmosphere having excess silver ions (the so-called reverse precipitation process) can also be used. A process wherein the pAg in the liquid phase where a silver halide is to be formed is kept constant, that is, the so-called controlled double-jet process, can be used as one type of double-jet process. According to the controlled double-jet process, a silver halide emulsion wherein the crystal form is regular and the grain sizes are nearly uniform can be obtained.

Into the silver halide emulsion used in the present invention, various polyvalent metal ion impurities can be introduced during the formation or physical ripening of the emulsion grains. Examples of such compounds to be used include salts of cadmium, zinc, lead, copper, and thallium, and salts or complex salts of an element of Group VIII, such as iron, ruthenium, rhodium, palladium, osmium, iridium, and platinum. Particularly the elements of Group VIII can be preferably used. Although the amount of these compounds to be added varies over a wide range according to the purpose, preferably the amount is $10^{-9}$ to $10^{-2}$ mol for the silver halide.

The silver halide emulsion used in the present invention is generally chemically sensitized and spectrally sensitized.

As the chemical sensitization method, sulfur sensitization, wherein typically an unstable sulfur compound is added, noble metal sensitization, represented by gold sensitization, or reduction sensitization can be used alone or in combination. As the compounds used in the chemical sensitization, preferably those described in JP-A No. 215272/1987, page 18 (the right lower column) to page 22 (the right upper column), are used.

The spectral sensitization is carried out for the purpose of providing the emulsions of the layers of the photographic material of the present invention with spectral sensitivities in desired wavelength regions. In the present invention, the spectral sensitization is preferably carried out by adding dyes that absorb light in the wavelength ranges corresponding to the desired spectral sensitivities, that is, by adding spectrally sensitizing dyes. As the spectrally sensitizing dyes used herein, for example, those described by F. M. Harmer in "Heterocyclic compounds—Cyanine dyes and related compounds" (published by John Wiley & Sons [New York, London], 1964) can be mentioned. As specific examples of the compounds and the spectral sensitization method, those described in the above JP-A No. 215272/1987, page 22 (the right upper column) to page 38, are preferably used.

In the silver halide emulsion used in the present invention, various compounds or their precursors can be added for the purpose of stabilizing the photographic performance or preventing fogging that will take place during the process of the production of the photographic material, or during the storage or photographic processing of the photographic material. As specific examples of these compounds, those described in the above-mentioned JP-A No. 215272/1987, pages 39 to 72, are preferably used.

As the emulsion used in the present invention, use is made of a so-called surface-sensitive emulsion, wherein a latent image is formed mainly on the grain surface, or of a so-called internal-image emulsion, wherein a latent image is formed mainly within the grains.

When the present invention is used for color photographic materials, generally in the color photographic material are used a yellow coupler, a magenta coupler, and a cyan coupler, which will couple with the oxidized product of the aromatic amine color-developing agent to form yellow, magenta, and cyan.

Cyan couplers, magenta couplers, and yellow couplers preferably used in combination with the coupler of the present invention are those represented by the following formulae (C-I), (C-II), (M-I), (M-II), and (Y):

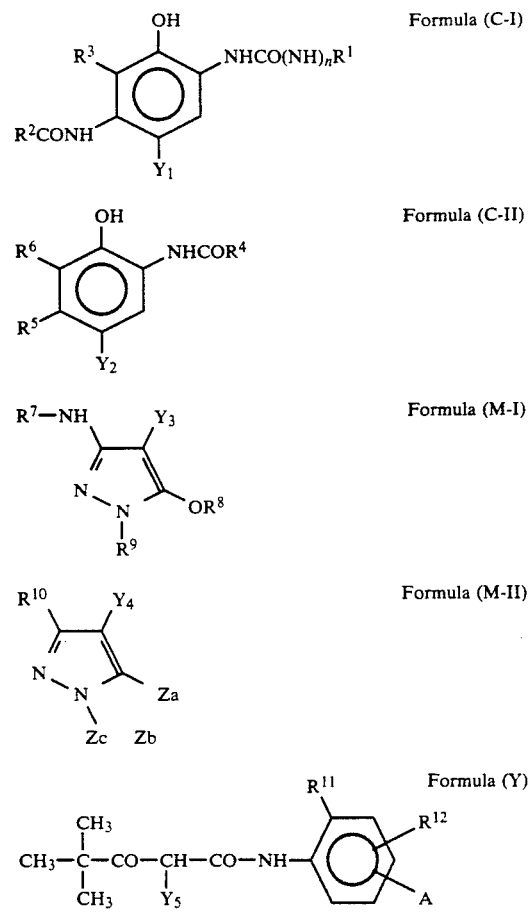

In formulae (C-I) and (C-II), $R^1$, $R^2$, and $R^4$ each represent a substituted or unsubstituted aliphatic, aromatic, or heterocyclic group, $R^3$, $R^5$, and $R^6$ each represent a hydrogen atom, a halogen atom, an aliphatic group, an aromatic group, or an acylamino group, $R^3$ and $R^2$ together may represent a group of nonmetallic atoms to form a 5- or 6-membered ring, $Y_1$ and $Y_2$ each represent a hydrogen atom or a group that is capable of coupling off with the oxidation product of a developing agent, and n is 0 or 1.

In formula (C-II), $R^5$ preferably represents an aliphatic group such as a methyl group, an ethyl group, a propyl group, a butyl group, a pentadecyl group, a tert-butyl group, a cyclohexyl group, a cyclohexylmentyl group, a phenylthiomethyl group, a dodecyloxyphenylthiomethyl group, a butaneamidomethyl group, and a methoxymethyl group.

Preferable examples of the cyan couplers represented by formulae (C-I) and (C-II) are given below:

In formula (C-I), preferable $R^1$ is an aryl group or a heterocyclic group, and more preferably an aryl group substituted by a halogen atom, an alkyl group, an alkoxy group, an aryloxy group, an acylamino group, an acyl group, a carbamoyl group, a sulfonamido group, a sulfamoyl group, a sulfonyl group, a sulfamido group, an oxycarbonyl group, or a cyano group.

In formula (C-I), when $R^3$ and $R^2$ together do not form a ring, $R^2$ is preferably a substituted or unsubstituted alkyl group, or aryl group, and particularly preferably an alkyl group substituted by a substituted aryloxy, and preferably $R^3$ represents a hydrogen atom.

In formula (C-II), preferable $R^4$ is a substituted or unsubstituted alkyl group or aryl group, and particularly preferably an alkyl group substituted by a substituted aryloxy group.

In formula (C-II), preferable $R^5$ is an alkyl group having 2 to 15 carbon atoms, or a methyl group substituted by a substituent having 1 or more carbon atoms, and the substituent is preferably an arylthio group, an alkylthio group, an acylamino group, an aryloxy group, or an alkyloxy group.

In formula (C-II), preferable $R^5$ is an alkyl group having 2 to 15 carbon atoms, and particularly preferably an alkyl group having 2 to 4 carbon atoms.

In formula (C-II), preferable $R^6$ is a hydrogen atom or a halogen atom, and particularly preferably a chlorine atom or a fluorine atom. In formulae (C-I) and (C-II), preferable $Y_1$ and $Y_2$ each represent a hydrogen atom, a halogen atom, an alkoxy group, an aryloxy group, an acyloxy group, or a sulfonamido group.

In formula (M-I), $R^7$ and $R^9$ each represent an aryl group, $R^8$ represents a hydrogen atom, an aliphatic or aromatic acyl group, an aliphatic or aromatic sulfonyl group, and $Y_3$ represents a hydrogen atom or a coupling split-off group. Allowable substituents of the aryl group represented by $R^7$ and $R^9$ are the same substituents as those acceptable to the substituent $R^1$, and if there are two substituents, they may be the same or different. $R^8$ is preferably a hydrogen atom, an aliphatic acyl group, or a sulfonyl group, and particularly preferably a hydrogen atom. Preferably $Y_3$ is of the type that will split-off at one of a sulfur atom, an oxygen atom, and a nitrogen atom, and particularly preferably the sulfur atom will split-off as described, for example, in U.S. Pat. No. 4,351,897 and International Publication Patent No. WO 88/04795.

In formula (M-II), $R^{10}$ represents a hydrogen atom or a substituent. $Y_4$ represents a hydrogen atom or a coupling split-off group, and particularly preferably a halogen atom or an arylthio group. Za, Zb, and Zc each represent methine, a substituted methine, =N—, or —NH—, and one of the Za—Zb bond and the Zb—Zc bond is a double bond, and the other is a single bond. If the Zb—Zc bond is a carbon-carbon double bond, it may be part of the aromatic ring. A dimer or more higher polymer formed through $R^{10}$ or $Y_4$ is included, and if Za, Zb, or Zc is a substituted methine, a dimer or more higher polymer formed through that substituted methine is included.

Of the pyrazoloazole couplers represented by formula (M-II), imidazo[1,2-b]pyrazoles described in U.S. Pat. No. 4,500,630 are preferable in view of reduced yellow subsidiary absorption of the color-formed dye and light-fastness, and pyrazolo[1,5-b][1,2,4] triazoles described in U.S. Pat. No. 4,540,654 are particularly preferable.

Further, use of pyrazolotriazole couplers wherein a branched alkyl group is bonded directly to the 2-, 3-, or 6-position of a pyrazolotriazole ring, as described in JP-A No. 65245/1976, pyrazoloazole couplers containing a sulfonamido group in the molecule, as described in JP-A No. 65246/1986, pyrazoloazole couplers having an alkoxyphenylsulfonamido ballasting group, as described in JP-A No. 147254/1986, and pyrazolotriazole couplers having an aryloxy group or an alkoxy group in the 6-position, as described in European Patent (Publication) Nos. 226,849 and 294,785, is preferable.

In formula (Y), $R^{11}$ represents a halogen atom, an alkoxy group, a trifluoromethyl group, or an aryl group, and $R^{12}$ represents a hydrogen atom, a halogen atom, or an alkoxy group. A represents —NHCOR$^{13}$,

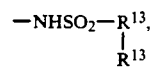

—SO$_2$NHR$^{13}$, —COOR$^{13}$, or

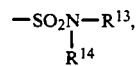

wherein $R^{13}$ and $R^{14}$ each represent an alkyl group, an aryl group, or an acyl group. $Y_5$ represents a coupling split-off group. Substituents of $R^{12}$, $R^{13}$, and $R^{14}$ are the same as those acceptable to $R^1$, and the coupling split-off group $Y_5$ is of the type that will split off preferably at an oxygen atom or a nitrogen atom, and particularly preferably it is of the nitrogen atom split-off type.

Specific examples of couplers represented by formulae (C-I), (C-II), (M-I), (M-II) and (Y) are listed below.

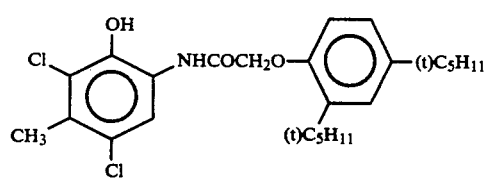

(C-1)

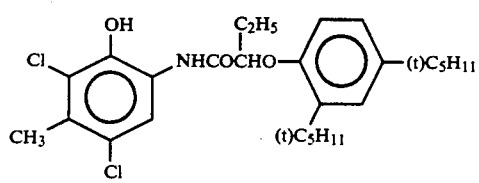

(C-2)

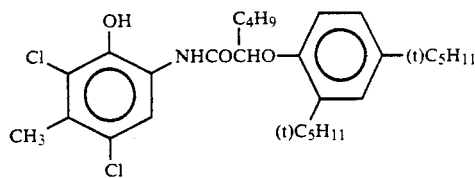
(C-3)
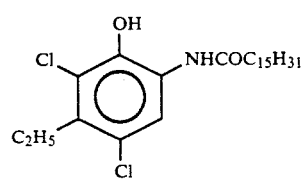
(C-4)
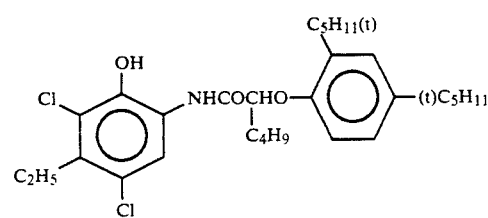
(C-5)
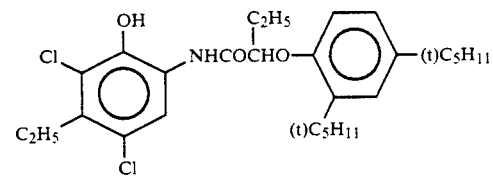
(C-6)
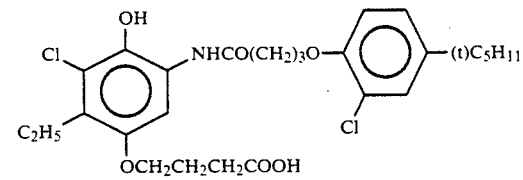
(C-7)
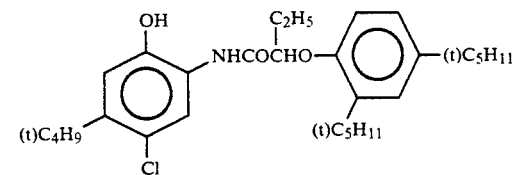
(C-8)
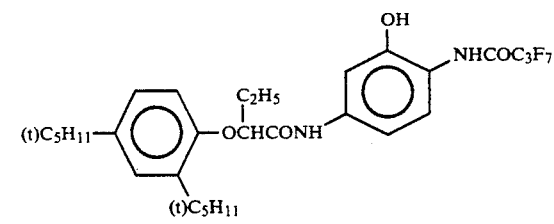
(C-9)
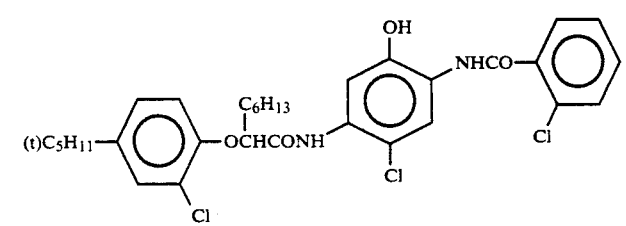
(C-10)

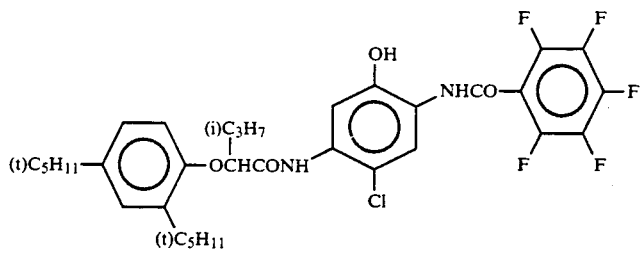
(C-11)
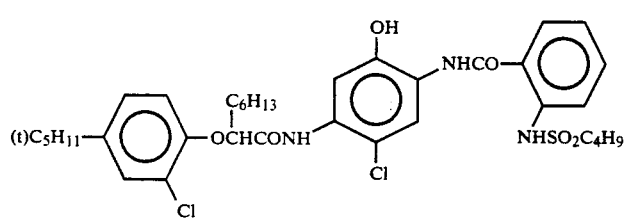
(C-12)
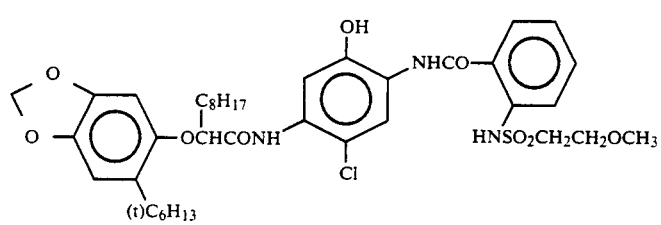
(C-13)
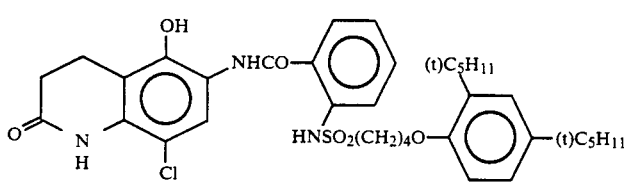
(C-14)
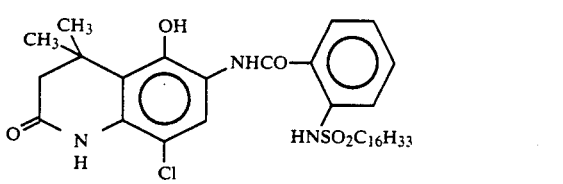
(C-15)
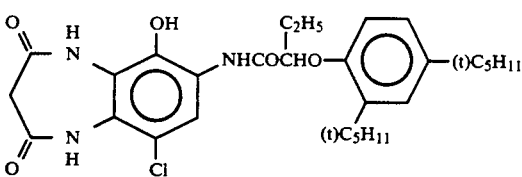
(C-16)
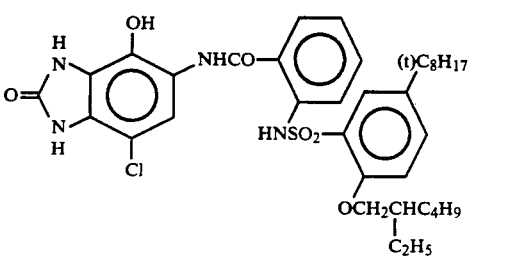
(C-17)

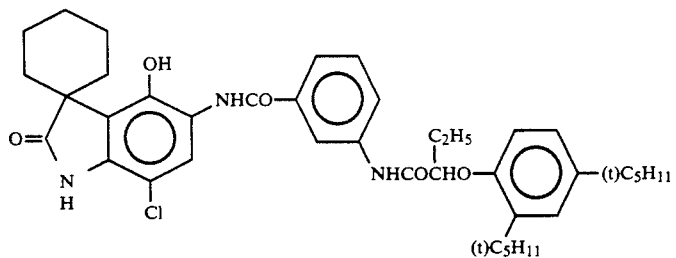
(C-18)
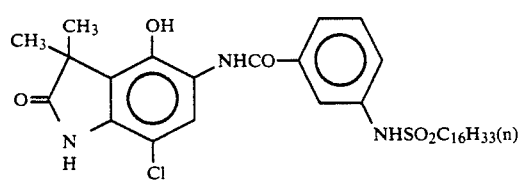
(C-19)
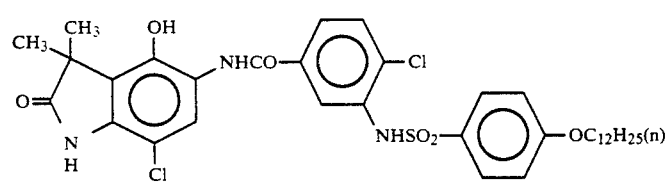
(C-20)
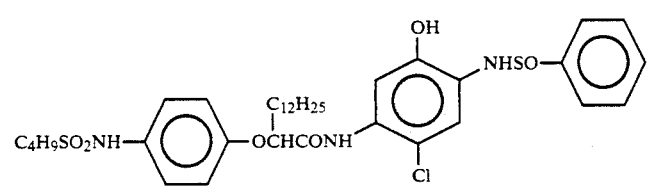
(C-21)
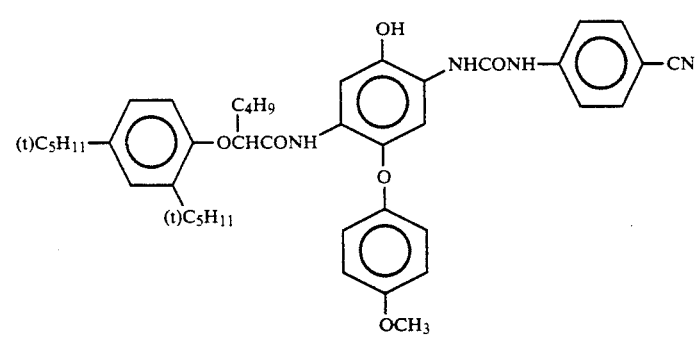
(C-22)
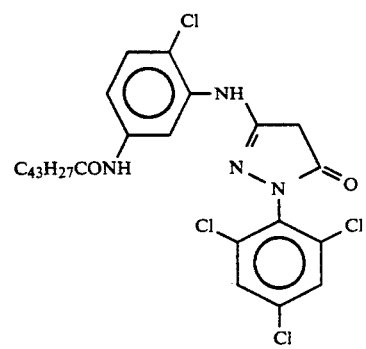
(M-1)

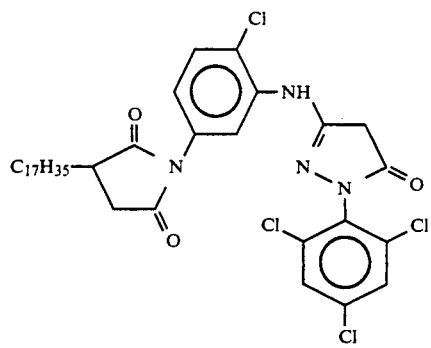
(M-2)
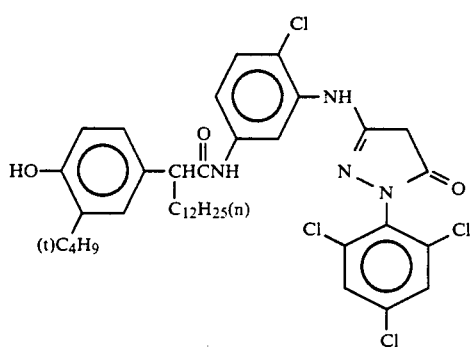
(M-3)
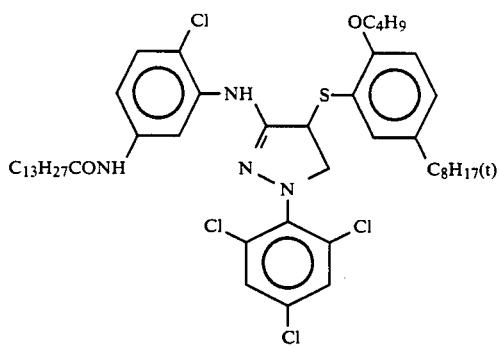
(M-4)
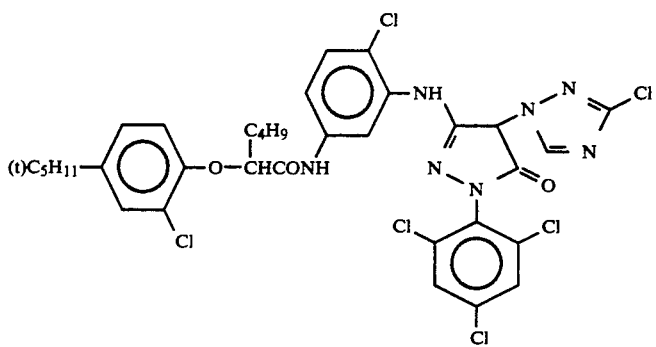
(M-5)

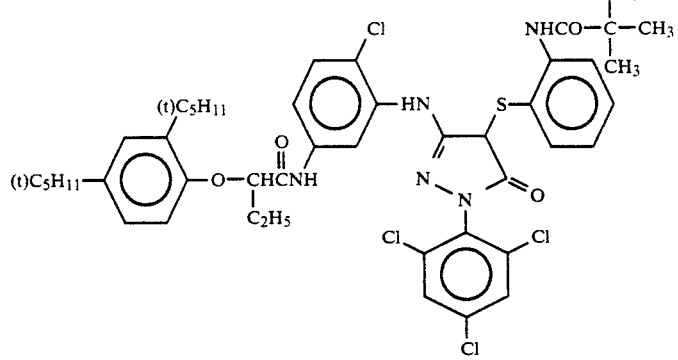
(M-6)
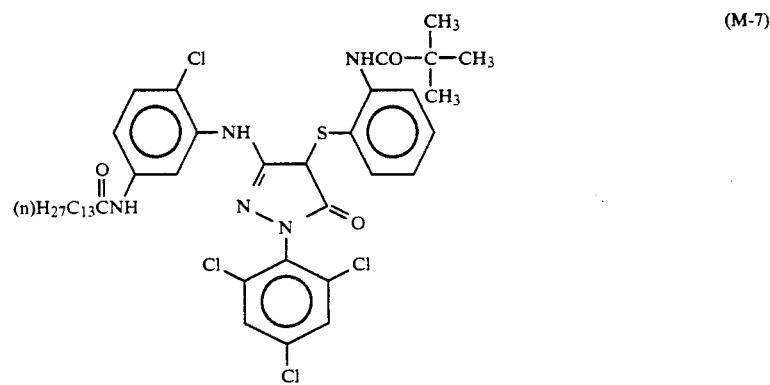
(M-7)
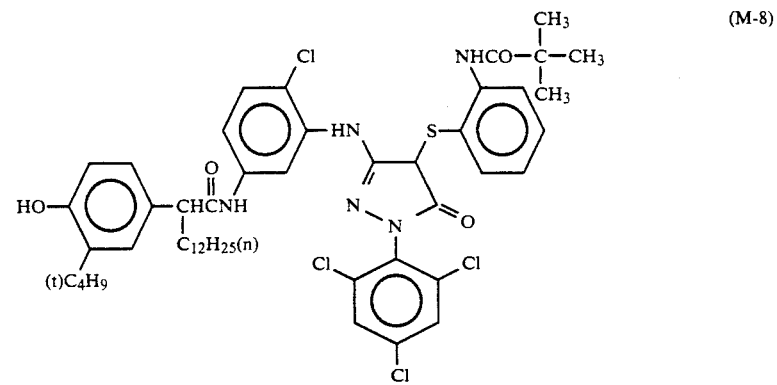
(M-8)

| Compound | R₁₀ | R₁₅ | Y₄ |
|---|---|---|---|

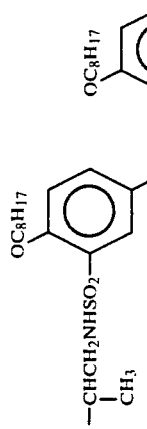

Structure:

$R_{10}$—pyrazole ring with $Y_4$, NH, and $R_{15}$ substituents

M-9: R₁₀ = CH₃—; R₁₅ = -CH(CH₃)CH₂NHSO₂-aryl (with OC₈H₁₇ and C₈H₁₇(t) substituents); Y₄ = Cl M-10: R₁₀ = The same as the above; R₁₅ = -CH(CH₃)CH₂NHSO₂-aryl (with OCH₂CH₂OC₆H₁₃(n) and C₈H₁₇(t)); Y₄ = The same as the above M-11: R₁₀ = (CH₃)₃C—; R₁₅ = -CH(CH₃)CH₂NHCOCH(C₂H₅)-aryl (with C₅H₁₁(t) groups); Y₄ = 4-methylphenyl (—⌬—CH₃)

M-12: R₁₀ = 2-methoxyphenoxy (OCH₃ substituted phenoxy); R₁₅ = aryl-NHSO₂-aryl (with OC₈H₁₇, C₈H₁₇(t), and tolyl); Y₄ = 2,5-disubstituted phenyl with OC₄H₉, —S—, and C₈H₁₇(t)

-continued

| Compound | $R_{10}$ | $R_{15}$ | $Y_4$ |
|---|---|---|---|
| M-13 | $CH_3$ | ![structure: -CH(CH₃)CH₂NHSO₂-phenyl(OC₂H₄OC₂H₅)-NHSO₂-phenyl(OC₈H₁₇)(C₈H₁₇(t))] | Cl |
| M-14 | The same as the above | ![structure: -CH(-CCH₃₂-CH₂NHCOCHO-C₆H₁₃(n))-phenyl(C₅H₁₁(t))(C₅H₁₁(t))] | The same as the above |
| M-15 | The same as the above | ![structure: -CH(CH₃)CH₂NHCOCHO-C₆H₁₃(n)-phenyl(C₅H₁₁(t))(C₅H₁₁(t))] | The same as the above |
| M-16 | The same as the above | ![structure: -CHCH₂NHCO-phenyl(OC₁₂H₂₅(n)) with CH₃] | The same as the above |
| M-17 | The same as the above | ![structure: -CHCH₂NHCO-phenyl(OC₁₆H₃₃(n)) with CH₃] | The same as the above |

-continued

| Compound | $R_{10}$ | $R_{15}$ | $Y_4$ |
|---|---|---|---|
| M-18 | phenyl-OCH₂CH₂O— | 4-OCH₃-phenoxy-phenyl; —CH₂CH₂NHSO₂-(2-OC₈H₁₇, 5-C₈H₁₇(t))phenyl | 2-OC₄H₉-5-C₈H₁₇(t)-phenyl-S— |
| M-19 | CH₃CH₂O— | The same as the above | The same as the above |
| M-20 | 4-O(CH₂)₂O—phenyl (*); 2-OC₈H₁₇-5-C₈H₁₇(t)-phenyl-SO₂NH— (*) | 2,4-dichlorophenyl | Cl |
| M-21 | 2-OCH₃-phenoxy | —CH(CH₃)CH₂NHSO₂-(2-OC₈H₁₇(n), 5-C₈H₁₇(t))phenyl | 2-OC₄H₉-5-C₈H₁₇(t)-phenyl-S— (same as above) |

$$\begin{array}{c} R_{10}\text{—pyrazolotriazole ring with } Y_4, R_{15}, NH \end{array}$$

-continued

| Compound | $R_{10}$ | $R_{15}$ | $Y_4$ |
|---|---|---|---|
| M-22 | $CH_3-$ | HO—⟨phenyl⟩—$SO_2$—⟨phenyl⟩—$OCH(C_{10}H_{21})CONH$—⟨phenyl⟩—$(CH_2)_{\overline{2}}$ | Cl |
| M-23 | The same as the above | $(n)C_6H_{13}$, $(n)C_8H_{17}$ — $CHCH_2SO_2$–$(CH_2)_{\overline{2}}$ | The same as the above |
| M-24 | $(CH_3)_2CH-$ | $OC_4H_9$—⟨phenyl with $SO_2$–$(CH_2)_{\overline{2}}$ and $C_8H_{17}(t)$⟩ | The same as the above |
| M-25 | $+CH-CH_2)_{\overline{50}}+CH_2-C)_{\overline{50}}$ with $COOCH_2CH_2OCH_3$, $CH_3$, $CONH-$ | $CH_3-CH-CH_2NHSO_2CH_3$ | The same as the above |
| M-26 | ⟨phenyl⟩—O— | $+(CH_2)_2NHSO_2$—⟨phenyl with $OC_8H_{17}$ and $C_8H_{17}(t)$⟩ | The same as the above |
| M-27 | $CH_3-$ | ⟨2,4,6-trimethylphenyl with $NHCOCHO(n)C_{10}H_{21}$⟩—$SO_2$—⟨phenyl⟩—$OCH_2$—⟨phenyl⟩ | Cl |

-continued
| Compound | R₁₀ | R₁₅ | Y₄ |
|---|---|---|---|
| M-28 | (CH₃)₃C— | 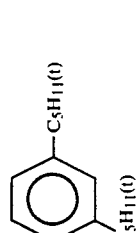 | The same as the above |
| M-29 | 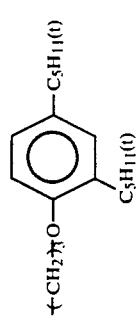 | 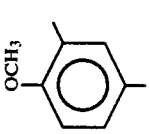 | The same as the above |
| M-30 | CH₃— |  | The same as the above |

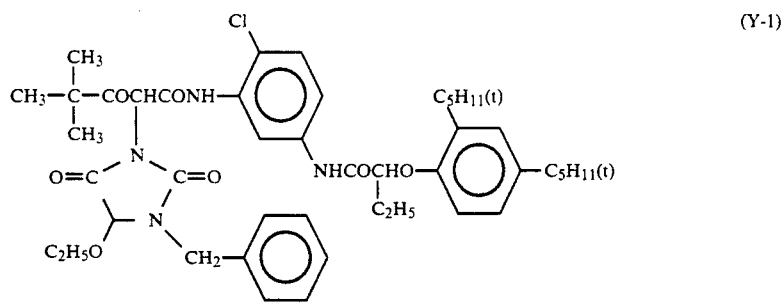
(Y-1)
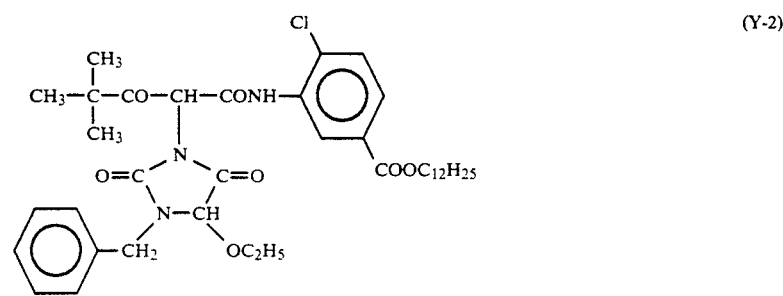
(Y-2)
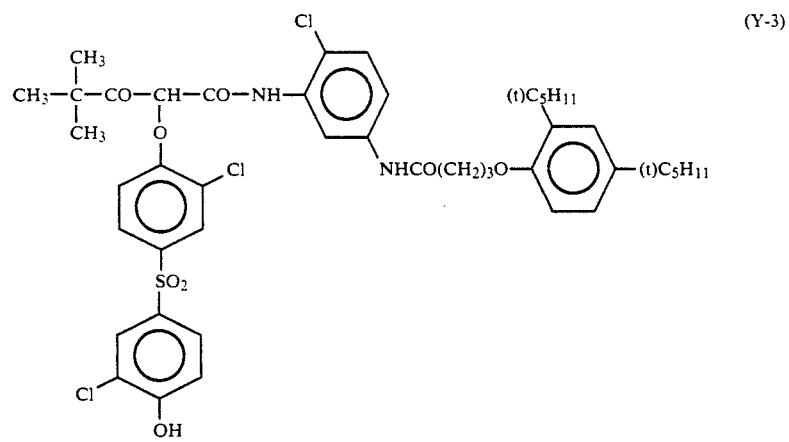
(Y-3)
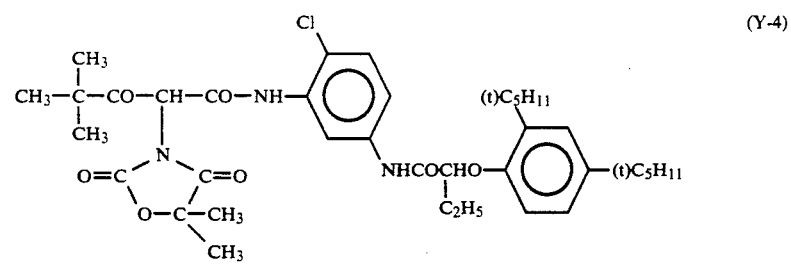
(Y-4)
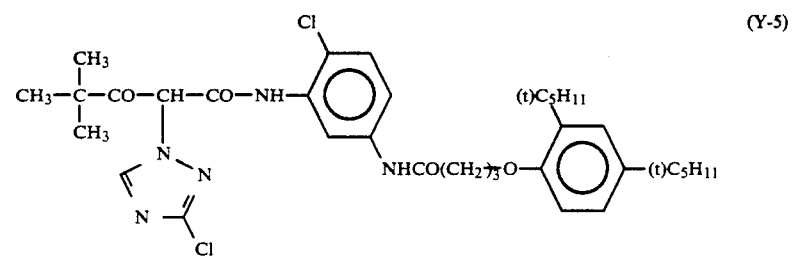
(Y-5)

-continued

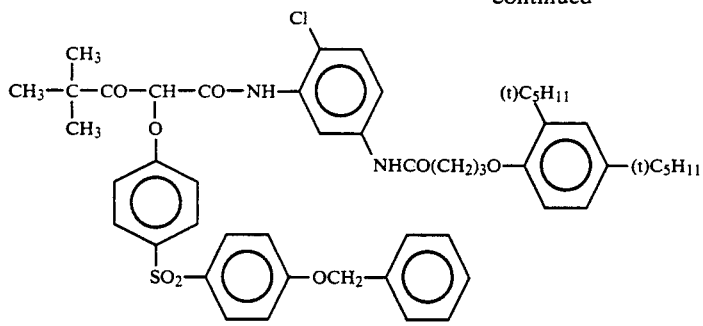 (Y-6)

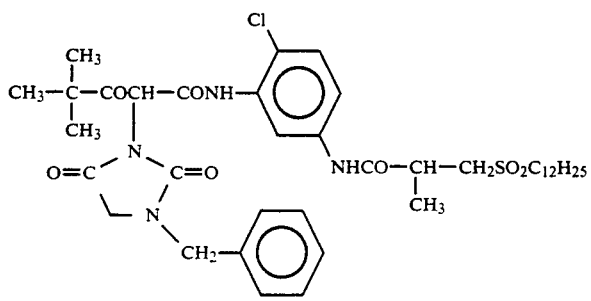 (Y-7)

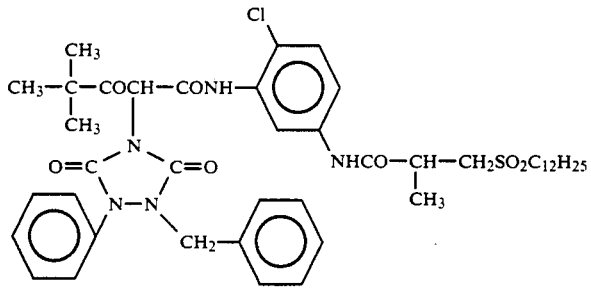 (Y-8)

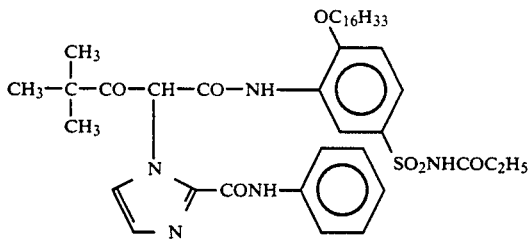 (Y-9)

The couplers represented by formulae (C-I) to (Y) are contained in the silver halide emulsion layer constituting the photographic layer generally in an amount of 0.1 to 1.0 mol, preferably 0.1 to 0.5 mol, per mol of the silver halide.

In the present invention, in order to add the coupler to the photographic layer, various known techniques can be applied. Generally, the oil-in-water dispersion method known, as the oil-protect method, can be used for the addition, that is, after the coupler is dissolved in a solvent, it is emulsified and dispersed into an aqueous gelatin solution containing a surface-active agent. Alternatively, it is also possible that the coupler solution containing a surface-active agent can be added to water or an aqueous gelatin solution to form an oil-in-water dispersion with phase reversal of the emulsion. In the case of an alkali-soluble coupler, it can be dispersed by the so-called Fisher dispersion method. It is also possible that the low-boiling organic solvent can be removed from the coupler dispersion by means of distillation, noodle washing, ultrafiltration, or the like, followed by mixing with the photographic emulsion.

As the dispersion medium for the couplers, it is preferable to use a high-boiling organic solvent and/or a water-insoluble polymer compound having a dielectric constant of 2 to 20 (25° C.) and a refractive index of 1.5 to 1.7 (25° C.).

As the high-boiling organic solvent for the coupler of the present invention and other couplers, a high-boiling organic solvent represented by the following formula (A'), (B'), (C'), (D'), or (E') is preferably used.

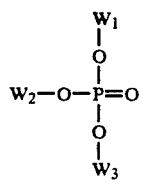   Formula (A')

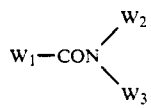

Formula (B')

$W_1-COOW_2$

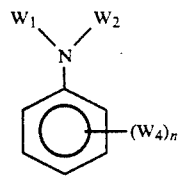

Formula (C')

Formula (D')

$W_1-O-W_2$     Formula (E')

wherein $W_1$, $W_2$, and $W_3$ each represent a substituted or unsubstituted alkyl group, cycloalkyl group, alkenyl group, aryl group or heterocyclic group, $W_4$ represents $W_1$, $OW_1$ or $S-W_1$, n is an integer of 1 to 5, when n is 2 or over, $W_4$ groups may be the same or different, and in formula (E'), $W_1$ and $W_2$ may together form a condensed ring.

As the high-boiling organic solvent used in the present invention, any compound other than compounds represented by formulae (A') to (E') can also be used if the compound has a melting point of 100° C. or below and a boiling point of 140° C. or over, and if the compound is incompatible with water and is a good solvent for the coupler. Preferably the melting point of the high-boiling organic solvent is 80° C. or below. Preferably the boiling point of the high-boiling organic solvent is 160° C. or over, and more preferably 170° C. or over.

Details of these high-boiling organic solvents are described in JP-A No. 215272/1987, page 137 (the right lower column) to page 144 (the right upper column).

The couplers can also be emulsified and dispersed into an aqueous hydrophilic colloid solution by impregnating them into a loadable latex polymer (e.g., U.S. Pat. No. 4,203,716) in the presence or absence of the above-mentioned high-boiling organic solvent, or by dissolving them in a polymer insoluble in water and soluble in organic solvents.

Preferably, homopolymers and copolymers described in International Publication Patent No. WO 88/00723, pages 12 to 30, are used, and particularly the use of acrylamide polymers is preferable because, for example, dye images are stabilized.

The photographic material that is prepared by using the present invention may contain, a color antifoggant, for example, a hydroquinone derivative, an aminophenol derivative, a gallic acid derivative, or an ascorbic acid derivative.

In the photographic material of the present invention, various anti-fading agent (discoloration preventing agent) can be used. That is, as organic anti-fading additives for cyan, magenta and/or yellow images, hydroquinones, 6-hydroxychromans, 6-hydroxycoumarans, spirochromans, p-alkoxyphenols, hindered phenols, including bisphenols, gallic acid derivatives, methylenedioxybenzenes, aminophenols, hindered amines, and ether or ester derivatives obtained by silylating or alkylating the phenolic hydroxyl group of these compounds can be mentioned typically. Metal complexes such as (bissalicylaldoximato)nickel complex and (bis-N,N-dialkyldithiocarbamato)nickel complexes can also be used.

Specific examples of the organic anti-fading agents are described in the following patent specifications:

Hydroquinones are described, for example, in U.S. Pat. Nos. 2,360,290, 2,418,613, 2,700,453, 2,701,197, 2,728,659, 2,732,300, 2,735,765, 3,982,944, and 4,430,425, British Patent No. 1,363,921, and U.S. Pat. Nos. 2,710,801 and 2,816,028; 6-hydroxychromans, 5-hydroxycoumarans, and spirochromans are described, for example, in U.S. Pat. Nos. 3,432,300, 3,573,050, 3,574,627, 3,698,909, and 3,764,337 and JP-A No. 152225/1987; spiroindanes are described in U.S. Pat. No. 4,360,589; p-alkoxyphenols are described, for example, in U.S. Pat. No. 2,735,765, British Patent No. 2,066,975, JP-A No. 10539/1984, and JP-B No. 19765/1982; hindered phenols are described, for example, in U.S. Pat. No. 3,700,455, JP-A No. 72224/1977, U.S. Pat. No. 4,228,235, and JP-B No. 6623/1977; gallic acid derivatives, methylenedioxybenzenes, and aminophenols are described, for example, in U.S. Pat. Nos. 3,457,079 and 4,332,886, and JP-B No. 21144/1981 respectively; hindered amines are described, for example, in U.S. Pat. Nos. 3,336,135, 4,268,593, British Patent Nos. 1,326,889, 1,354,313, and 1,410,846, JP-B No. 1420/1976, and JP-A Nos. 114036/1983, 53846/1984, and 78344/1984; and metal complexes are described, for example, in U.S. Pat. Nos. 4,050,938 and 4,241,155 and British Patent 2,027,731(A). To attain the purpose, these compounds can be added to the photosensitive layers by coemulsifying them with the corresponding couplers, with the amount of each compound being generally 5 to 100 wt. % for the particular coupler. To prevent the cyan dye image from being deteriorated by heat, and in particular light, it is more effective to introduce an ultraviolet absorber into the cyan color-forming layer and the opposite layers adjacent to the cyan color-forming layers.

As the ultraviolet absorber, aryl-substituted benzotriazole compounds (e.g., those described in U.S. Pat. No. 3,533,794), 4-thiazolidone compounds (e.g., those described in U.S. Pat. Nos. 3,314,794 and 3,352,681), benzophenone compounds (e.g., those described in JP-A No. 2784/1971), cinnamic acid ester compounds (e.g., those described in U.S. Pat. Nos. 3,705,805 and 3,707,395), butadiene compounds (e.g., those described in U.S. Pat. No. 4,045,229), or benzoxazole compounds (e.g., those described in U.S. Pat. Nos. 3,406,070, 3,677,672, and 4,271,207) can be used. Ultraviolet-absorptive couplers (e.g., α-naphthol type cyan dye forming couplers) and ultraviolet-absorptive polymers can, for example, be used also. These ultraviolet-absorbers may be mordanted in a particular layer.

In particular, the above-mentioned aryl-substituted benzotriazole compounds are preferable.

In the present invention, together with the above couplers, in particular together with the pyrazoloazole coupler, the following compounds are preferably used.

That is, it is preferred that a compound (F), which will chemically bond to the aromatic amide developing agent remaining after the color-developing process, to form a chemically inactive and substantially colorless compound, and/or a compound (G), which will chemically bond to the oxidized product of the aromatic amide color developing agent remaining after the color-developing process, to form a chemically inactive and substantially colorless compound, are used simultaneously or separately, for example, to prevent the occurrence of stain due to the formation of a color-developed dye by the reaction of the couplers with the color-developing agent remaining in the film during storage after the processing or with the oxidized product of the color-developing agent, and to prevent other side effects.

Preferable a compound (F) are those that can react with p-anisidine a the second-order reaction-specific rate k2 (in trioctyl phosphate at 80° C.) in the range of 1.0 l/mol sec to $1 \times 10^{-5}$ l/mol.sec. The second-order reaction- specific rate can be determined by the method described in JP-A No. 158545/1983.

If k2 is over this range, the compound itself becomes unstable, and in some cases the compound reacts with gelatin or water to decompose. On the other hand, if $k_2$ is below this range, the reaction with the remaining aromatic amine developing agent becomes slow, resulting, in some cases, in the failure to prevent the side effects of the remaining aromatic amine developing agent, which prevention is aimed at by the present invention.

More preferable as compound (F) are those that can be represented by the following formula (FI) or (FII):

Formula (FI)

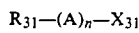
$R_{31}-(A)_n-X_{31}$

Formula (FII)

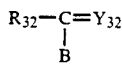
$R_{32}-C=Y_{32}$
$\quad\ |$
$\quad\ B$ wherein $R_{31}$ and $R_{32}$ each represent an aliphatic group, an aromatic group, or a heterocyclic group, n is 1 or 0, A represents a group that will react with an aromatic amine developing agent to form a chemical bond therewith, $X_{31}$ represents a group that will react with the aromatic amine developing agent and split off, B represents a hydrogen atom, an aliphatic group, an aromatic group, a heterocyclic group, an acyl group, or a sulfonyl group, Y represents a group that will facilitate the addition of the aromatic amine developing agent to the compound represented by formula (FII), and $R_{31}$ and $X_{31}$, or $Y_{32}$ and $R_{32}$ or B, may bond together to form a ring structure.

Of the processes wherein compound (F) bonds chemically to the remaining aromatic amine developing agent, typical processes are a substitution reaction and an addition reaction.

Specific examples of the compounds represented by formulae (FI), and (FII) are described, for example, in JP-A Nos. 158545/1988, 28338/1987, 2042/1989, and 86139/1989.

On the other hand, more preferable examples of compound (G), which will chemically bond to the oxidized product of the aromatic amine developing agent remaining after color development processing, to form a chemically inactive and colorless compound, can be represented by the following formula (GI):

Formula (GI)

$R_{33}-Z_{33}$ wherein $R_{33}$ represents an aliphatic group, an aromatic group, or a heterocyclic group, $Z_{33}$ represents a nucleophilic group or a group that will decompose in the photographic material to release a nucleophilic group.

Preferably the compounds represented by formula (GI) are ones wherein Z represents a group whose Pearson's nucleophilic $^nCH_3I$ value (R. G. Pearson, et al., *J. Am. Chem. Soc.*, 90, 319 (1968)) is 5 or over, or a group derived therefrom.

Specific examples of compounds represented by formula (GI) are described, for example, in European Published Patent No. 255722, JP-A Nos. 143048/1987, 229145/1987, 230039/1989, and 57259/1989, and European Published Patent Nos. 298321 and 277589.

Details of combinations of compound (G) and compound (F) are described in European Published Patent No. 277589.

The photographic material prepared in accordance with the present invention may contain, in the hydrophilic colloid layer, water-soluble dyes as filter dyes or to prevent irradiation, and for other purposes. Such dyes include oxonol dyes, hemioxonol dyes, styryl dyes, merocyanine dyes, cyanine dyes, and azo dyes. Among others, oxonol dyes, hemioxonol dyes, and merocyanine dyes are useful.

As a binder or a protective colloid that can be used in the emulsion layers of the present photographic material, gelatin is advantageously used, but other hydrophilic colloids can be used alone or in combination with gelatin.

In the present invention, gelatin may be lime-treated gelatin or acid-processed gelatin. Details of the manufacture of gelatin is described by Arthur Veis in *The Macromolecular Chemistry of Gelatin* (published by Academic Press, 1964).

As a base to be used in the present invention, a transparent film, such as cellulose nitrate film, and polyethylene terephthalate film or a reflection-type base that is generally used in photographic materials can be used. The use of a reflection-type base is more preferable.

The "reflection base" is one that enhances reflectivity, thereby making sharper the dye image formed in the silver halide emulsion layer, and it includes one having a base coated with a hydrophobic resin containing a dispersed light- reflective substance, such as titanium oxide, zinc oxide, calcium carbonate, and calcium sulfate, and also a base made of a hydrophobic resin containing a dispersed light- reflective substance. For example, there can be mentioned baryta paper, polyethylene-coated paper, polypropylene- type synthetic paper, a transparent base having a reflective layer, or additionally using a reflective substance, such as glass plate, polyester films of polyethylene terephthalate, cellulose triacetate, or cellulose nitrate, polyamide film, polycarbonate film, polystyrene film, and vinyl chloride resin.

As the other reflection base, a base having a metal surface of mirror reflection or secondary diffuse reflection may be used. A metal surface having a spectral reflectance in the visible wavelength region of 0.5 or more is preferable and the surface is preferably made to show diffuse reflection by roughening the surface or by using a metal powder. The surface may be a metal plate, metal foil or metal thin layer obtained by rolling, vapor deposition or galvanizing of metal such as, for example, aluminum, tin, silver, magnesium and alloy thereof. Of these, a base obtained by vapor deposition of metal is preferable. It is preferable to provide a layer of water resistant resin, in particular, a layer of thermoplastic resin. The opposite side to metal surface side of the base according to the present invention is preferably provided with an antistatic layer. The details of such base are described, for example, in JP-A Nos. 210346/1986, 24247/1988, 24251/1988 and 24255/1988.

It is advantageous that, as the light-reflective substance, a white pigment is kneaded well in the presence of a surface-active agent, and it is preferable that the surface of the pigment particles has been treated with a divalent to tetravalent alcohol.

The occupied area ratio (%) per unit area prescribed for the white pigments finely divided particles can be obtained most typically by dividing the observed area into contiguous unit areas of 6 $\mu m \times 6$ $\mu m$, and measuring the occupied area ratio (%) (Ri) of the finely divided particles projected onto the unit areas. The deviation coefficient of the occupied area ratio (%) can be obtained based on the ratio $s/\overline{R}$, wherein s stands for the standard deviation of Ri, and $\overline{R}$ stands for the average value of Ri. Preferably, the number (n) of the unit areas to be subjected is 6 or over. Therefore, the deviation coefficient $s/\overline{R}$ can be obtained by $$\sqrt{\frac{\sum\limits_{i=1}^{n} (R_i - R)^2}{n - 1}} \Bigg/ \frac{\sum\limits_{i=1}^{n} R_i}{n}$$

In the present invention, preferably the deviation coefficient of the occupied area ratio (%) of the finely divided particles of a pigment is 0.15 or below, and particularly 0.12 or below. If the variation coefficient is 0.08 or below, it can be considered that the substantial dispersibility of the particles is substantially "uniform."

Preferably, the color developer used for the development processing of the photographic material of the present invention is an aqueous alkaline solution whose major component is an aromatic primary amine derivative. As the aromatic primary amine derivative, aminophenol compounds are useful, though p-phenylene diamine compounds are preferably used, and typical examples thereof include 3-methyl-4-amino-N,N-diethylaniline, 3-methyl-4-amino-N-ethyl-N-$\beta$-hydroxyethylaniline, 3-methyl-4-amino-N-ethyl-N-$\beta$-methanesulfonamidoethylaniline, 4-amino-N-ethyl-N-$\beta$-hydroxyethylaniline, and 3-methyl-4-amino-N-ethyl-N-$\beta$-methoxyethylaniline, and their sulfates, hydrochlorides, and p-toluenesulfonates. A combination of two or more of these compounds may be used in accordance with the purpose.

The color developer generally contains, for example, buffers, such as carbonates or phosphates of alkali metals, and development inhibitors or antifoggants, such as bromide salts, iodide salts, benzimidazoles, benzothiazoles, or mercapto compounds. The color developer may, if necessary, contain various preservatives, such as hydroxylamine, diethylhydroxylamine, sulfites, hydrazines for example N,N-biscarboxymethylhydrazine, phenylsemicarbazides, triethanolamine, and catecholsulfonic acids, organic solvents such as ethylene glycol and diethylene glycol, development accelerators such as benzyl alcohol, polyethylene glycol, quaternary ammonium salts, and amines, dye forming couplers, competing couplers, auxiliary developers such as 1-phenyl-3-pyrazolidone, tackifiers, and various chelate agents as represented by aminopolycarboxylic acids, aminopolyphosphonic acids, alkylphosphonic acids, and phosphonocarboxylic acids, typical example thereof being ethylenediaminetetraacetic acid, nitrilotriacetic acid, diethylenetriaminepentaacetic acid, cyclohexanediaminetetraacetic acid, hydroxyethyliminodiacetic acid, 1-hydroxyethylidene-1,1-diphosphonic acid, nitrilo-N,N,N-trimethylenephosphonic acid, ethylenediamine-N,N,N',N'-tetramethylenephosphonic acid, and ethylenediamine-di(o-hydroxyphenylacetic acid), and their salts.

If reversal processing is carried out, it is common that after black and white development and reversal processing are carried out, the color development is carried out. As the black and white developers, known black and white developing agents, such as dihydroxybenzenes, for example hydroquinone, 3-pyrazolidones, for example 1-phenyl-3-pyrazolidone, and aminophenols, for example N-methyl-p-aminophenol, can be used alone or in combination.

Generally the pH of this color developer and black-and-white developing solution is 9 to 12. The replenishing amount of these developing solutions is generally 3 l or below per square meter of the color photographic material to be processed, though the replenishing amount changes depending on the type of color photographic material, and if the concentration of bromide ions in the replenishing solution is lowered previously, the replenishing amount can be lowered to 500 ml or below per square meter of the color photographic material. If it is intended to lower the replenishing amount, it is preferable to prevent the evaporation of the solution and oxidation of the solution with air by reducing the area of the solution in processing tank that is in contact with the air. The contact area of the photographic processing solution with the air in the processing tank is represented by the open surface ratio which is defined as follows:

$$\text{Open surface ratio (cm}^{-1}) = \frac{\text{Contact surface area (cm}^2) \text{ of the processing solution with the air}}{\text{Whole volume (cm}^3) \text{ of the processing solution}}$$

wherein "contact surface area of the processing solution with the air" means the surface area of the processing solution that is not covered by anything such as floating lids or rolls.

The open surface ratio is preferably 0.1 cm$^{-1}$ or less, more preferably 0.001 to 0.05 cm$^{-1}$.

Methods for reducing the open surface ratio that can be mentioned include the utilization of movable lids as described in JP-A NO. 241342/1987 and a slit-developing process as described in JP-A No. 216050/1988, besides a method of providing a closing materials such as floating lids.

It is preferable to adopt means for reducing the open surface ratio not only in a color developing a black-and-white developing process but also in all succeeding processes, such as bleaching, bleach-fixing, fixing, washing, and stabilizing processes.

It is also possible to reduce the replenishing amount by using means of suppressing the accumulation of bromide ions in the developer.

Although the processing time of color developing is settled, in generally, between 2 and 5 minutes, the time can be shortened by, for example, processing at high temperature and at high pH, and using a color developer having high concentration of color developing agent.

The photographic emulsion layers are generally subjected to a bleaching process after color development.

The beaching process can be carried out together with the fixing process (bleach-fixing process), or it can be carried out separately from the fixing process. Further, to quicken the process bleach-fixing may be carried out after the bleaching process. In accordance with the purpose, the process may be arbitrarily carried out using a bleach-fixing bath having two successive tanks, or a fixing process may be carried out before the bleach-fixing process, or a bleaching process. As the bleaching agent, use can be made of, for example, compounds of polyvalent metals, such as iron (III). As a typical bleaching agent, use can be made of organic complex salts of iron (III), such as complex salts of aminopolycarboxylic acids, for example ethylenediaminetetraacetic acid, diethylenetriaminetetraacetic acid, cyclohexanediaminetetraacetic acid, methyliminodiacetic acid, 1,3-diaminopropanetetraacetic acid, and glycoletherdiaminetetraacetic acid, citric acie, tartaric acid, and malic acid. Of these, aminopolycarboxylic acid iron (III) complex salts, including ethylenediaminetetraacetic acid iron (III) complex salts are preferable in view of rapid-processing and the prevention of pollution problem. Further, aminopolycarboxylic acid iron (III) complex salts are particularly useful in a bleaching solution as well as a bleach-fixing solution. The pH of the bleaching solution or the bleach-fixing solution using these aminopolycarboxylic acid iron (III) complex salts is generally 4.0 to 8.0, by if it is required to quicken the process, the process can be effected at a low pH.

In the bleaching solution, the bleach-fixing solution, and the bath preceding them a bleach-accelerating agent may be used if necessary. Examples of useful bleach-accelerating agents are compounds having a mercapto group or a disulfide linkage, described in U.S. Pat. No. 95630/1978, and Research Disclosure No. 17129 (July, 1978); thiazolidine derivatives, described in JP-A No. 140129/1975; thiourea derivatives, described in U.S. application Ser. No. 3,706,561; iodide salts, described in JP-A No. 16235/1983; polyoxyethylene compounds in West German Patent No. 2,748,460; polyamine compounds, described in JP-B No. 8836/1970; and bromide ions. Of these, compounds having a mercapto group or a disulfide group are preferable in view of higher acceleration effect, and in particular, compounds described in U.A. Patent No. 3,893,858, West German Patent No. 1,290,812, and JP-A No. 95630/1978 are preferable. Compounds described in U.S. Pat. No. 4,552,834 are preferable. These bleach-accelerating agents may be added into a photographic material. When the color photographic materials for photography are to be bleach-fixed, these bleach-accelerating agents are particularly effective.

As a fixing agent can be mentioned thiosulfates, thiocyanates, thioether-type compounds, thioureas, and large amounts of iodide salts, although thiosulfate is used usually, and in particular ammonium thiosulfate is widely used. As the preservative for bleach-fix solution sulfite salt, bisulfite salt, or carbonyl-bisulfite adduct is preferable.

It is common for the silver halide color photographic material of the present invention to undergo, after a desilvering process such as fixing or bleach-fix, a washing step and/or a stabilizing step. The amount of washing water may be set within a wide range depending on the characteristics (e.g., due to the materials used, such as couplers), the application of the photographic material, the washing temperature, the number of washing tanks (the number of steps), the type of replenishing system, including, for example, the counter-current system and the direct flow system and other various conditions. Of these, the relationship between the number of water-washing tanks and the amount of washing water in the multi-stage counter current system can be found according to the method described in *Journal of Society of Motion Picture and Television Engineers*, Vol. 64, pages 248 to 253 (May 1955).

According to the multi-stage-counter-current system described in the literature mentioned above, although the amount of washing water can be considerably reduced, bacteria propagate with an increase of retention time of the washing water in the tanks, leading to a problem with the resulting suspended matter adhering to the photographic material. In processing the present color photographic material, as a measure to solve this problem the method of reducing calcium and magnesium described in JP-A No. 288838/1987 can be used quite effectively. Also chlorine-type bactericides such as sodium chlorinated isocyanurate, cyabendazoles, isothiazolone compounds described in JP-A No. 8542/1982, benzotriazoles, and other bactericides described by Hiroshi Horiguchi in *Bokin Bobai-zai no Kagaku*, (1986) published by Sankyo-Shuppan, *Biseibutsu no mekkin, Sakkin, Bobaigijutsu* (1982) edited by Eiseigijutsu-kai, published by Kogyo-Gijutsu-kai, and in *Bokin Bobaizai Jiten* (1986) edited by Nihon Bokin Bobai-gakkai, can be used.

The pH of the washing water used in processing the present photographic material is 4 to 9, preferably 5 to 8. The washing water temperature and the washing time to be set may very depending, for example, on the characteristics and the application of the photographic material, and they are generally selected in the range of 15° to 45° C. for sec to 10 min, and preferably in the range of 25° to 40° C. for 30 sec to 5 min. Further, the photographic material of the present invention can be processed directly with a stabilizing solution instead of the above washing. In such a stabilizing process, any of known processes, for example, a multi-step counter-current stabilizing process or its low-replenishing-amount process, described in JP-A Nos. 8543/1982, 14834/1983, and 220345/1985.

In some cases, the above washing process is further followed by a stabilizing process, and as an example thereof can be mentioned a stabilizing bath that is used as a final bath for color photographic materials for photography, which contains formalin and a surface-active agent. In this stabilizing bath, each kind of the chelating agents and bactericides may be added.

The over-flow solution due to the replenishing of washing solution and/or stabilizing solution may be reused in other steps, such as a desilvering step.

The silver halide color photographic material of the present invention may contain therein a color-developing agent for the purpose of simplifying and quickening the process. To contain such a color-developing agent, it is preferable to use a precursor for color-developing agent. For example, indoaniline-type compounds described in U.S. Pat. No. 3,342,597, Schiff base-type compounds described in U.S. Pat. No. 3,342,599 and *Research Disclosure* Nos. 14850 and 15159, aldol compounds described in *Research Disclosure* No. 13924, and metal salt complexes described in U.S. Pat. No. 3,719,492, and urethane-type compounds described in JP-A No. 135628/1978 can be mentioned.

For the purpose of accelerating the color development, the present silver halide color photographic material may contain, if necessary, various 1-phenyl-3-pyrazolicones. Typical compounds are described in JP-A Nos. 64339/1981, 144547/1982, and 115438/1983.

The various processing solutions used for the present invention may be used at 10° to 50° C. Although generally a temperature of 33° to 38° C. may be standard, a higher temperature can be used to accelerate the process to reduce the processing time, or a lower temperature can be used to improve the image quality or the stability of the processing solution. Also, to save the silver of the photographic material, a process using hydrogen peroxide intensification or cobalt intensification described in West German Patent No. 2,226,770 and U.S. Pat. No. 3,674,499 may be carried out.

When compounds of the present invention are used, color images less in subsidiary absorption, good in color reproduction, and excellent in fastness can be obtained.

As is apparent from the Synthesis Examples, compounds of the present invention can be synthesized from inexpensive raw materials in four steps, which is a small number and advantageous in view of the cost.

Next, the present invention will be described in detail in accordance with examples, but the invention is not limited to them.

EXAMPLE 1

A multilayer photographic material was prepared by multi-coatings composed of the following layer composition on an under-coated cellulose triacetate base. Coating solutions were prepared as follows:

Preparation of the Emulsion Layer Coating Solution

To a mixture of 1.85 mmol of cyan coupler and 10 ml of ethyl acetate, tricresyl phosphate (Solvent) in an amount of equal weight of the cyan coupler was added and dissolved. The resulting solution was dispersed and emulsified in 38 g of 14% aqueous gelatin solution containing 3 ml of 10% dodecylbenzenesulfonate solution. Separately silver chlorobromide emulsion (silver bromide: 70.0 mol %) was prepared and sulfur sensitized, and then this emulsion and the above-obtained emulsified dispersion were mixed together and dissolved to give the solution.

Composition of Layers

The composition of each layer used in this experiment is shown below (the figures represent coating amount per m$^2$).

| Supporting Base | |
|---|---|
| Cellulose triacetate base | |
| Silver emulsion layer | |
| Silver chlorobromide emulsion (above-described) | 8.0 mmol |
| Coupler | 1.0 mmol |
| Solvent (the same coating amount as the coupler) | |
| Gelatin | 5.2 g |
| Protective layer | |
| Gelatin | 1.3 g |
| Acryl-modified copolymer of polyvinyl alcohol (modification degree: 17%) | 0.17 g |
| Liquid paraffin | 0.03 g |

The above-obtained photographic material was processed through the processing process shown below after an exposure to light image-wisely.

| Processing step | Temperature | Time |
|---|---|---|
| Color-developing | 33° C. | 3 min |
| Bleach-fixing | 33° C. | 2 min |
| Water-washing | 33° C. | 3 min |

The compositions of each processing solution were as follows:

| Color developer | |
|---|---|
| Water | 700 ml |
| Benzyl alcohol | 15 ml |
| Diethylene glycol | 10 ml |
| Sodium sulfite | 1.7 g |
| Potassium bromide | 0.6 g |
| Sodium hydrogencarbonate | 0.7 g |
| Potassium carbonate | 31.7 g |
| Hydroxylamine sulfate | 3.0 g |
| N-ethyl-N-(β-methanesulfonamidoethyl)-3-methyl-4-aminoaniline sulfate | 4.5 g |
| Fluorescent brightening agent (WHITEX-4, made by Sumitomo Chemical Ind.) | 1.0 g |
| Water to make | 1000 ml |
| pH | 10.25 |
| Bleach-fixing solution | |
| Water | 400 ml |
| Ammonium thiosulfate (70%) | 150 ml |
| Sodium sulfite | 18 g |
| Iron (III) ammonium ethylenediaminetetraacetate dihydrate | 55 g |
| Disodium ethylenediaminetetraacetate | 5 g |
| Water to make | 1000 ml |
| pH | 6.70 |

Samples 101 to 110 were prepared by using couplers shown in Table 1. Each coupler was exchanged in an equimolecular amount.

TABLE 1

| Sample | Coupler | Remarks |
|---|---|---|
| 101 | R-1 | Comparative Example |
| 102 | R-2 | Comparative Example |
| 103 | Exemplified compound (1) | This Invention |
| 104 | Exemplified compound (2) | This Invention |
| 105 | Exemplified compound (3) | This Invention |
| 106 | Exemplified compound (4) | This Invention |
| 107 | Exemplified compound (13) | This Invention |
| 108 | Exemplified compound (17) | This Invention |
| 109 | Exemplified compound (23) | This Invention |
| 110 | Exemplified compound (29) | This Invention |
| 111 | Exemplified compound (32) | This Invention |

(R-1): Conventional-type cyan Coupler

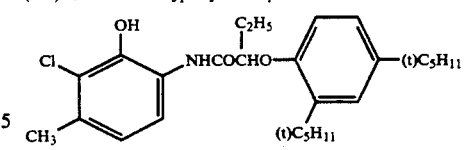

(R-2): Conventional-type cyan Coupler

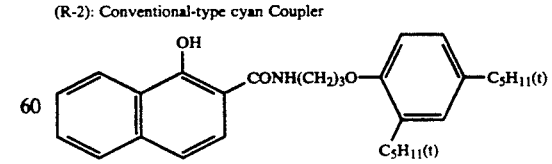

After development processing, the spectral absorption of maximum density part was measured to evaluate the hue by the wavelength of maximum absorption and the amount of subsidiary absorption given by the formula shown below.

$$\text{Amount of subsidiary absorption} = \frac{\text{(Absorption density at 425 nm)}}{\text{(Absorption density at wavelength of maximum absorption)}}$$

Results are shown in Table 2.

TABLE 2

| Sample | Coupler | Amount of Subsidiary Absorption |
|---|---|---|
| 101 | R - 1 | 0.13 |
| 102 | R - 2 | 0.15 |
| 103 | Exemplified compound (1) | 0.06 |
| 104 | Exemplified compound (2) | 0.07 |
| 105 | Exemplified compound (3) | 0.08 |
| 106 | Exemplified compound (4) | 0.06 |
| 107 | Exemplified compound (13) | 0.06 |
| 108 | Exemplified compound (17) | 0.07 |
| 109 | Exemplified compound (23) | 0.06 |
| 110 | Exemplified compound (29) | 0.05 |
| 111 | Exemplified compound (32) | 0.06 |

As is apparent from Table 2, it can be noticed that the coupler of the present invention is excellent in color reproduction with less subsidiary absorption.

Next, in order to evaluate image-dye fastness, each of processed samples was stored in dark at 60° C. for 3 months and in dark at 60° C. and relative humidity 70% for 45 days, and was subjected to radiation treatment of Xenon lamp (95,000 lux) for 150 hours.

In every case, an apparent lowering of density in Sample 101 and 102 was recognized, but the lowering of density in Samples 103 to 111 was almost not recognized. Thus, it was noticed that the cyan coupler of the present invention is excellent in image-dye fastness.

EXAMPLE 2

A multilayer photographic material was prepared by multi-coatings composed of the following layer composition on an under-coated cellulose triacetate base. Coating solutions were prepared as follows:

Preparation of the Emulsion Layer Coating Solution

To a mixture of 1.85 mmol of cyan coupler and 10 ml of ethyl acetate, tricresyl phosphate (Solvent) in an amount of equal weight of the cyan coupler was added and dissolved. The resulting solution was dispersed and emulsified in 33 g of 14% aqueous gelatin solution containing 3 ml of 10% dodecylbenzenesulfonate solution. Separately silver chlorobromide emulsion (containing 0.2 mol % of silver bromide being localized on the grain surface) was prepared and sulfur sensitized, and then this emulsion and the above-obtained emulsified dispersion were mixed together and dissolved to give the composition shown below, thereby preparing the coating solution.

Composition of Layers

The composition of each layer used in this experiment is shown below (the figures represent coating amount per m²).

| Supporting Base | |
|---|---|
| Cellulose triacetate base | |
| Silver emulsion layer | |
| Silver chlorobromide emulsion (above-described) | 2.0 mmol |
| Coupler | 0.5 mmol |
| Solvent (the same coating amount as the coupler) | |
| Gelatin | 5.2 g |
| Protective layer | |
| Gelatin | 1.3 g |
| Acryl-modified copolymer of polyvinyl alcohol (modification degree: 17%) | 0.17 g |
| Liquid paraffin | 0.03 g |

The above-obtained photographic material was processed through the processing process shown below after an exposure of light image-wisely.

| Processing step | Temperature | Time |
|---|---|---|
| Color-developing | 35° C. | 45 sec. |
| Bleach-fixing | 30-35° C. | 45 sec. |
| Rinsing (1) | 30-35° C. | 20 sec. |
| Rinsing (2) | 30-35° C. | 20 sec. |
| Rinsing (3) | 30-35° C. | 20 sec. |

The compositions of each processing solution were as follows:

| Color-developer | |
|---|---|
| Water | 800 ml |
| Ethylenediamine-N,N,N',N'-tetra-methylene phosphonic acid | 1.5 g |
| Triethanolamine | 8.0 g |
| Sodium chloride | 1.4 g |
| Potassium carbonate | 25.0 g |
| N-ethyl-N-(β-methanesulfonamidoethyl)-3-methyl-4-aminoaniline sulfate | 5.0 g |
| N'N-bis(carboxymethyl)hydrazine | 5.5 g |
| Fluorescent brightening agent (WHITEX-4, made by Sumitomo Chemical Ind.) | 1.0 g |
| Water to make | 1000 ml |
| pH | 10.05 |
| Bleach-fixing solution | |
| Water | 400 ml |
| Ammonium thiosulfate (70%) | 100 ml |
| Sodium sulfite | 17 g |
| Iron (III) ammonium ethylenediamine-tetraacetate dihydrate | 55 g |
| Disodium ethylenediaminetetraacetate | 5 g |
| Ammonium bromide | 40 g |
| Water to make | 1000 ml |
| pH | 6.70 |

Rinsing Solution

Ion-exchange water (each content of calcium and magnesium was 3 ppm)

Samples 201 to 211 were prepared by using couplers shown in Table 3. Each coupler was exchanged in an equimolecular amount.

TABLE 3

| Sample | Coupler | Remarks |
|---|---|---|
| 201 | R - 1* | Comparative Example |
| 202 | R - 2* | Comparative Example |
| 203 | Exemplified compound (1) | This Invention |
| 204 | Exemplified compound (2) | This Invention |
| 205 | Exemplified compound (3) | This Invention |
| 206 | Exemplified compound (4) | This Invention |
| 207 | Exemplified compound (13) | This Invention |
| 208 | Exemplified compound (17) | This Invention |
| 209 | Exemplified compound (23) | This Invention |
| 210 | Exemplified compound (29) | This Invention |
| 211 | Exemplified compound (32) | This Invention |

Note:
*the same as in Example 1

The color reproduction and image-dye fastness of each processed sample were evaluated in the same manner as in Example 1. Results shows that the coupler of the present invention is superior compared with comparative couplers.

EXAMPLE 3

A multilayer photographic material was prepared by multi-coatings composed of the following layer composition on a two-side polyethylene laminated paper support. Coating solutions were prepared as follows:

Preparation of the First Layer Coating Solution

To a mixture of 19.1 g of yellow coupler (ExY), 4.4 g of image-dye stabilizer (Cpd-1) and 0.7 g of image-dye stabilizer (Cpd-7), 27.2 ml of ethyl acetate and 8.2 g of solvent (Solv-1) were added and dissolved. The resulting solution was dispersed and emulsified in 185 ml of 10% aqueous gelatin solution containing 8 ml of sodium dodecylbenzenesulfonate. Separately another emulsion was prepared by adding two kinds of blue-sensitive sensitizing dye, shown below, to a blend of silver chlorobromide emulsions (cubic grains, 3:7 (silver mol ratio) blend of grains having 0.88 μm and 0.7 μm of average grain size, and 0.08 and 0.10 of deviation coefficient of grain size distribution, respectively, each in which 0.2 mol % of silver bromide was located at the surface of grains) in such amounts that each dye corresponds $2.0 \times 10^{-4}$ mol to the large size emulsion and $2.5 \times 10^{-4}$ mol to the small size emulsion, per mol of silver, and then sulfur-sensitized. The thus-prepared emulsion and the above-obtained emulsified dispersion were mixed together and dissolved to give the composition shown below, thereby preparing the first layer coating solution.

Coating solutions for the second to seventh layers were also prepared in the same manner as the first-layer coating solution. As a gelatin hardener for the respective layers, 1-hydroxy-3,5-dichloro-s-treazine sodium salt was used.

As spectral-sensitizing dyes for the respective layers, the following compounds were used:

Blue-sensitive Emulsion Layer

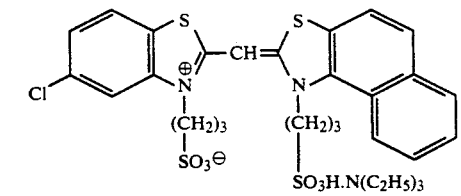

and

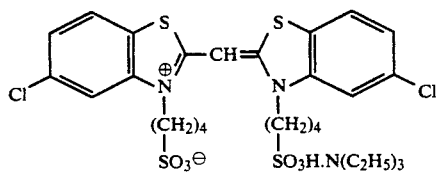

(each $2.0 \times 10^{-4}$ mol to the large size emulsion and $2.5 \times 10^{-4}$ mol to the small size emulsion, per mol of silver halide.)

Green-sensitive Emulsion Layer

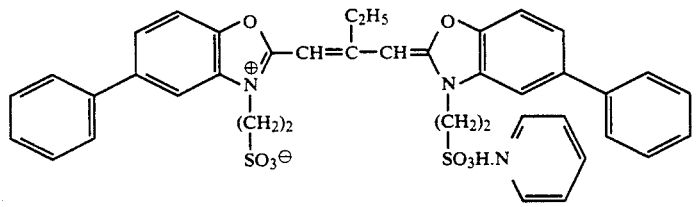

($4.0 \times 10^{-4}$ mol to the large size emulsion and $5.6 \times 10^{-4}$ mol to the small size emulsion, per mol of silver halide) and

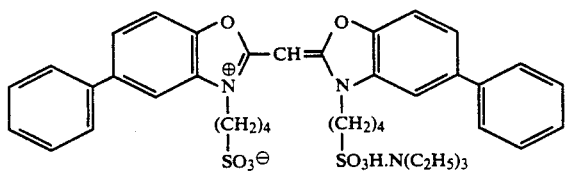

$7.0 \times 10^{-5}$ mol to the large size emulsion and $1.0 \times 10^{-5}$ mol to the small size emulsion, per mol of silver halide)

Red-sensitive Emulsion Layer

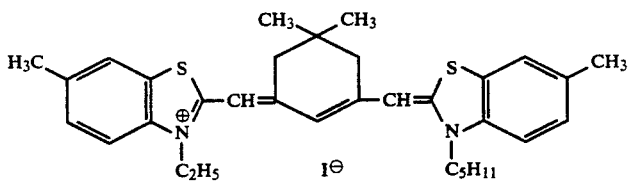

($0.9 \times 10^{-4}$ mol to the large size emulsion and $1.1 \times 10^{-4}$ mol to the small size emulsion, per mol of silver halide)

To the red-sensitive emulsion layer, the following compound was added in an amount of $2.6 \times 10^{-3}$ mol per mol of silver halide:

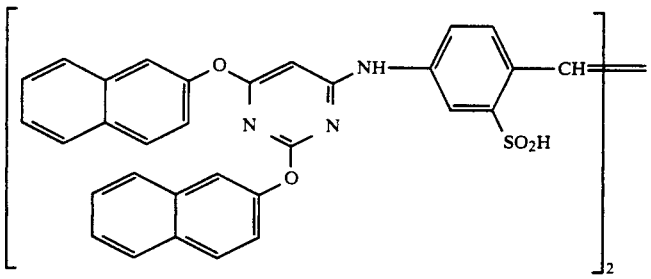

Further, 1-(5-methylureidophenyl)-5-mercaptotetrazole was added to the blue-sensitive emulsion layer, the green-sensitive emulsion layer, and the red-sensitive emulsion layer in amount of $8.5 \times 10^{-5}$ mol, $7.0 \times 10^{-4}$ mol, and $2.5 \times 10^{-4}$ mol, per mol of silver halide, respectively.

The dyes shown below were added to the emulsion layers for prevention of irradiation.

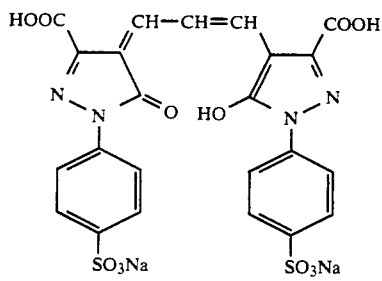

and

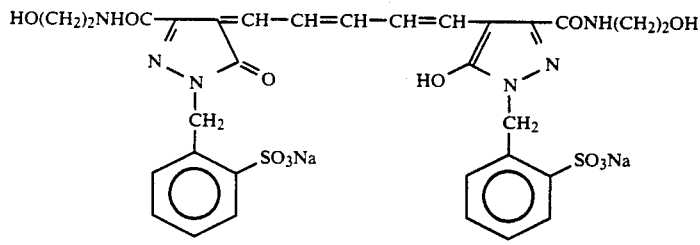

Composition of Layers

The composition of each layer is shown below. The figures represent coating amount (g/m²). The coating amount of each silver halide emulsion is given in terms of silver.

| Supporting Base | |
|---|---|
| Paper laminated on both sides with polyethylene (a white pigment, TiO₂, and a bluish dye, ultramarine, were included in the first layer side of the polyethylene-laminated film) | |
| First Layer (Blue-sensitive emulsion layer): | |
| The above-described silver chlorobromide emulsion | 0.30 |
| Gelatin | 1.86 |
| Yellow coupler (ExY) | 0.82 |
| Image-dye stabilizer (Cpd-1) | 0.19 |
| Solvent (Solv-1) | 0.35 |
| Image-dye stabilizer (Cpd-7) | 0.06 |
| Second Layer (Color-mix preventing layer): | |
| Gelatin | 0.99 |
| Color mix inhibitor (Cpd-5) | 0.08 |
| Solvent (Solv-1) | 0.16 |
| Solvent (Solv-4) | 0.08 |
| Third Layer (Green-sensitive emulsion layer): | |
| Silver chlorobromide emulsions (cubic grains, 1:3 (Ag mol ratio) blend of grains having 0.55 μm and 0.39 μm of average grain size, and 0.10 and 0.08 of deviation coefficient of grain size distribution, respectively, each in which 0.8 mol % of AgBr was located at the surface of grains) | 0.12 |
| Gelatin | 1.24 |
| Magenta coupler (ExM) | 0.20 |
| Image-dye stabilizer (Cpd-2) | 0.03 |
| Image-dye stabilizer (Cpd-3) | 0.15 |
| Image-dye stabilizer (Cpd-4) | 0.02 |
| Image-dye stabilizer (Cpd-9) | 0.02 |
| Solvent (Solv-2) | 0.40 |
| Fourth Layer (Ultraviolet absorbing layer): | |
| Gelatin | 1.58 |
| Ultraviolet absorber (UV-1) | 0.47 |
| Color-mix inhibitor (Cpd-5) | 0.05 |
| Solvent (Solv-5) | 0.24 |
| Fifth Layer (Red-sensitive emulsion layer): | |
| Silver chlorobromide emulsions (cubic grains, 1:4 (Ag mol ratio) blend of grains having 0.58 μm and 0.45 μm of average grain size, and 0.09 and 0.11 of deviation coefficient of grain size distribution, respectively, each in which 0.6 mol % of AgBr was located at the surface of grains) | 0.23 |
| Gelatin | 1.34 |
| Cyan coupler (cyan coupler) | 0.63 mmol |
| Image-dye stabilizer (Cpd-6) | 0.17 |
| Image-dye stabilizer (Cpd-7) | 0.40 |
| Image-dye stabilizer (Cpd-8) | 0.04 |
| Solvent (Solv-6) | 0.15 |

-continued

| Sixth layer (Ultraviolet ray absorbing layer): | |
|---|---|
| Gelatin | 0.53 |
| Ultraviolet absorber (UV-1) | 0.16 |
| Color-mix inhibitor (Cpd-5) | 0.02 |
| Solvent (Solv-5) | 0.08 |
| Seventh layer (Protective layer): | |
| Gelatin | 1.33 |
| Acryl-modified copolymer of polyvinyl alcohol (modification degree: 17%) | 0.17 |
| Liquid paraffin | 0.03 |

Compounds used are as follows:

(ExY) Yellow Coupler

Mixture (1:1 in molar ratio) of

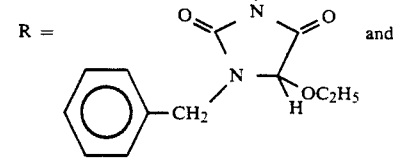 and

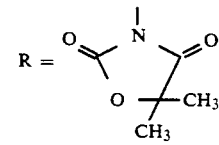

of the following formula

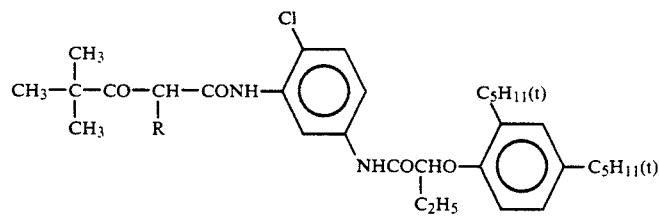

(ExM) Magenta Coupler

Mixture (1:1 in molar ratio) of

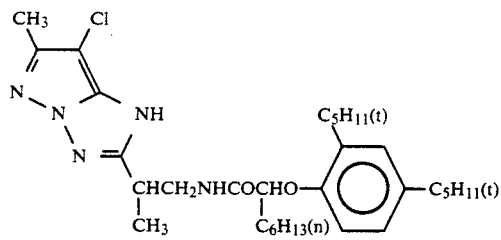

and

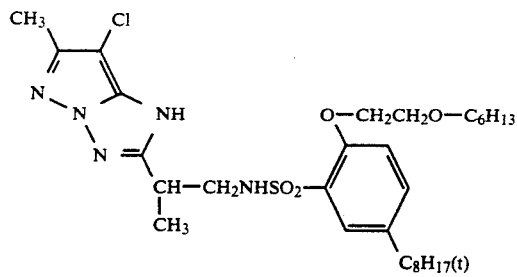

(Cpd-1) Image-dye stabilizer

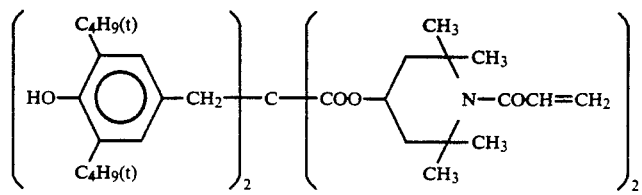

(Cpd-2) Image-dye stabilizer

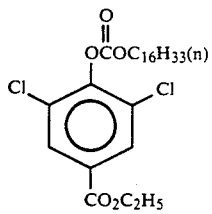
(Cpd-3) Image-dye stabilizer
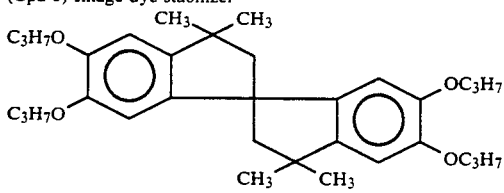
(Cpd-4) Image-dye stabilizer
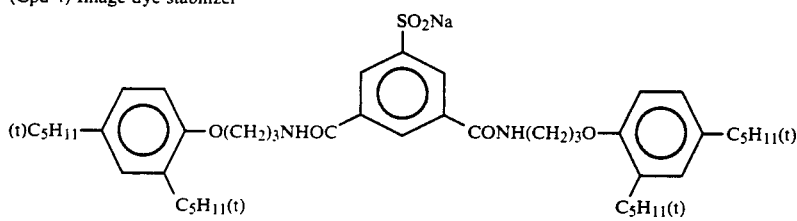
(Cpd-5) Color-mix inhibitor
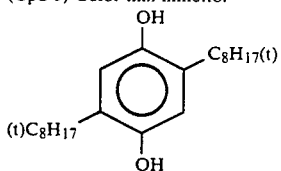
(Cpd-6) Image-dye stabilizer
Mixture (2:4:4 in weight ratio) of
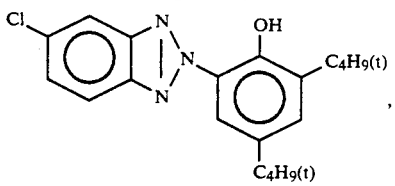
,
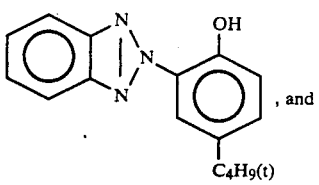
, and
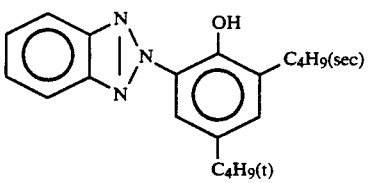
(Cpd-7) Image-dye stabilizer
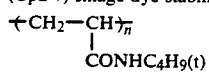
Average molecular weight: 60,000
(Cpd-8) Image-dye stabilizer

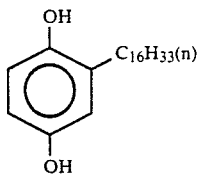
(Cpd-9) Image-dye stabilizer
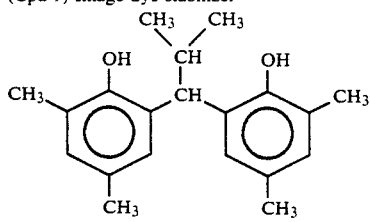
(UV-1) Ultraviolet ray absorber
Mixture (4:2:4 in weight ratio) of
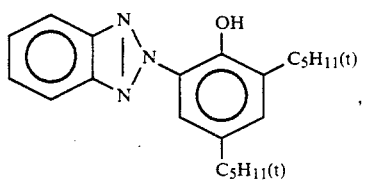
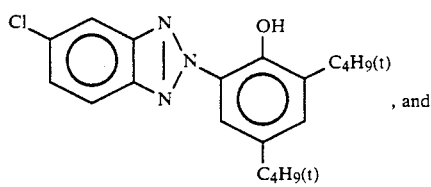
, and
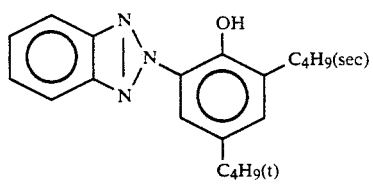
(Solv-1) Solvent
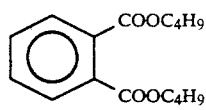
(Solv-2) Solvent
Mixture (2:1 in volume ratio) of
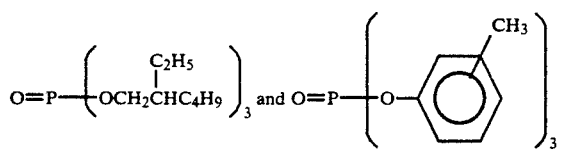
(Solv-4) Solvent
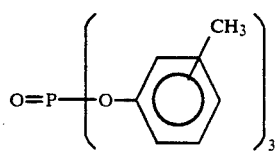
(Solv-5) Solvent

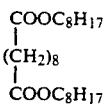

(Solv-6) Solvent

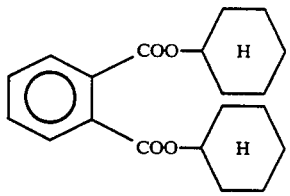

First, each sample was subjected to an exposure to light image-wisely. After exposure to light, each sample was subjected to a continuous processing (running test) according to the processing process shown below by using a paper processor, until the replenishing amount reached to twice the tank volume of color developer.

| Processing step | Temperature | Time | Replenisher | Tank Volume |
|---|---|---|---|---|
| Color developing | 35° C. | 45 sec. | 161 ml | 17 l |
| Bleach-fixing | 30-35° C. | 45 sec. | 215 ml | 17 l |
| Rinsing (1) | 30-35° C. | 20 sec. | — | 10 l |
| Rinsing (2) | 30-35° C. | 20 sec. | — | 10 l |
| Rinsing (3) | 30-35° C. | 20 sec. | 350 ml | 10 l |
| Drying | 70-80° C. | 60 sec. | | |

Note:
*Replenisher amount per m² of photographic material. Rinsing steps were carried out in 3-tanks countercurrent mode from the tank of rinsing (3) toward the tank of rinsing (1).

The composition of each processing solution is as followed, respectively:

| | Tank Solution | Replenisher |
|---|---|---|
| Color-developer | | |
| Water | 800 ml | 800 ml |
| Ethylenediamine-N,N,N',N'-tetra-methylene phosphonic acid | 1.5 g | 2.0 g |
| Triethanolamine | 8.0 g | 12.0 g |
| Sodium chloride | 1.4 g | — |
| Potassium carbonate | 25 g | 25 g |
| N-ethyl-N-(β-methanesulfonamidoethyl)-3-methyl-4-aminoaniline sulfate | 5.0 g | 7.0 g |
| N,N-Bis(carboxymethyl)hydrazine | 5.5 g | 7.0 g |
| Fluorescent whitening agent (WHITEX-4B, made by Sumitomo Chemical Ind.) | 1.0 g | 2.0 g |
| Water to make | 1000 ml | 1000 ml |
| pH | 10.05 | 10.55 |
| Bleach-fixing solution | | |
| (Both tank solution and replenisher) | | |
| Water | 400 ml | |
| Ammonium thiosulfate (70%) | 100 ml | |
| Sodium sulfite | 17 g | |
| Iron (III) ammonium ethylenediamine-tetraacetate | 55 g | |
| Disodium ethylenediaminetetraacetate | 5 g | |
| Ammonium bromide | 40 g | |
| Water to make | 1000 ml | |
| pH | 6.0 | |
| Rinsing solution | | |
| (Both tank solution and replenisher) | | |
| Ion-exchanged water (calcium and magnesium each are 3 ppm or below) | | |

Samples 301 to 311 were prepared by using couplers shown in Table 4.

TABLE 4

| Sample | Cyan Coupler | Remarks |
|---|---|---|
| 301 | R - 1* | Comparative Example |
| 302 | R - 2* | Comparative Example |
| 303 | Exemplified compound (1) | This Invention |
| 304 | Exemplified compound (2) | This Invention |
| 305 | Exemplified compound (3) | This Invention |
| 306 | Exemplified compound (4) | This Invention |
| 307 | Exemplified compound (13) | This Invention |
| 308 | Exemplified compound (17) | This Invention |
| 309 | Exemplified compound (23) | This Invention |
| 310 | Exemplified compound (29) | This Invention |
| 311 | Exemplified compound (32) | This Invention |

After processing, each sample was evaluated in the same manner as in Examples 1 and 2. From the results, it is understood that the coupler of the present invention is excellent in color reproduction and image-dye fastness.

EXAMPLE 4

Multilayer color photographic material (Sample 401) was prepared by multi-coating of each layer having a composition shown below on an undercoated triacetate cellulose film base.

Composition of Photosensitive Layer

The figure corresponding to each component is indicated in coating amount of g/m², hut the coating amount of silver halide emulsion is indicated in terms of silver. With respects to the sensitizing dye, the coating amount is indicated in mol per mol of silver halide in the same layer.

| (Sample 401) | | |
|---|---|---|
| First layer (Halation preventing layer) | | |
| Black colloidal silver | silver | 0.18 |
| Gelatin | | 1.40 |
| Second layer (Intermediate layer) | | |
| 2,5-Di-t-pentadecylhydroquinin | | 0.18 |
| EX-1 | | 0.07 |
| EX-3 | | 0.02 |
| EX-12 | | 0.002 |
| U-1 | | 0.06 |
| U-2 | | 0.08 |
| U-3 | | 0.10 |
| HBS-1 | | 0.10 |
| HBS-2 | | 0.02 |
| Gelatin | | 1.04 |
| Third layer (First red-sensitive emulsion layer) | | |
| Emulsion A | silver | 0.25 |
| Emulsion B | silver | 0.25 |
| Sensitizing dye I | | $6.9 \times 10^{-5}$ |
| Sensitizing dye II | | $1.8 \times 10^{-5}$ |
| Sensitizing dye III | | $3.1 \times 10^{-4}$ |
| EX-2 | | 0.335 |

| | | |
|---|---|---|
| EX-10 | | 0.020 |
| U-1 | | 0.07 |
| U-2 | | 0.05 |
| U-3 | | 0.07 |
| HBS-1 | | 0.060 |
| Gelatin | | 0.87 |
| Fourth layer (Second red-sensitive emulsion layer) | | |
| Emulsion G | silver | 1.0 |
| Sensitizing dye I | | $5.1 \times 10^{-5}$ |
| Sensitizing dye II | | $1.4 \times 10^{-5}$ |
| Sensitizing dye III | | $2.3 \times 10^{-4}$ |
| EX-2 | | 0.400 |
| EX-3 | | 0.050 |
| EX-10 | | 0.015 |
| U-1 | | 0.07 |
| U-2 | | 0.05 |
| U-3 | | 0.07 |
| Gelatin | | 1.30 |
| Fifth layer (Third red-sensitive emulsion layer) | | |
| Emulsion D | silver | 1.60 |
| Sensitizing dye I | | $5.4 \times 10^{-5}$ |
| Sensitizing dye II | | $1.4 \times 10^{-5}$ |
| Sensitizing dye III | | $2.4 \times 10^{-4}$ |
| EX-3 | | 0.010 |
| EX-4 | | 0.080 |
| EX-2 | | 0.097 |
| HBS-1 | | 0.22 |
| HBS-2 | | 0.10 |
| Gelatin | | 1.63 |
| Sixth layer (Intermediate layer) | | |
| EX-5 | | 0.040 |
| HBS-1 | | 0.020 |
| Gelatin | | 0.80 |
| Seventh layer (First green-sensitive emulsion layer) | | |
| Emulsion A | silver | 0.15 |
| Emulsion B | silver | 0.15 |
| Sensitizing dye V | | $3.0 \times 10^{-5}$ |
| Sensitizing dye VI | | $1.0 \times 10^{-5}$ |
| Sensitizing dye VII | | $3.8 \times 10^{-4}$ |
| EX-6 | | 0.260 |
| EX-1 | | 0.021 |
| EX-7 | | 0.030 |
| EX-8 | | 0.025 |
| HBS-1 | | 0.100 |
| HBS-3 | | 0.010 |
| Gelatin | | 0.63 |
| Eighth layer (Second green-sensitive emulsion layer) | | |
| Emulsion C | silver | 0.45 |
| Sensitizing dye V | | $2.1 \times 10^{-5}$ |
| Sensitizing dye VI | | $7.0 \times 10^{-5}$ |
| Sensitizing dye VII | | $2.6 \times 10^{-4}$ |
| EX-6 | | 0.094 |
| Ex-8 | | 0.018 |
| Ex-7 | | 0.026 |
| HBS-1 | | 0.160 |
| HBS-3 | | 0.008 |
| Gelatin | | 0.50 |
| Ninth layer (Third green-sensitive emulsion layer) | | |
| Emulsion D | silver | 1.2 |
| Sensitizing dye V | | $3.5 \times 10^{-5}$ |
| Sensitizing dye VI | | $8.0 \times 10^{-5}$ |
| Sensitizing dye VII | | $3.0 \times 10^{-4}$ |
| EX-13 | | 0.015 |
| EX-11 | | 0.100 |
| Ex-1 | | 0.025 |
| HBS-1 | | 0.25 |
| HBS-3 | | 0.10 |
| Gelatin | | 1.54 |
| Tenth layer (Yellow filter layer) | | |
| Yellow colloidal silver | silver | 0.05 |
| EX-5 | | 0.08 |
| HBS-1 | | 0.03 |
| Gelatin | | 0.95 |
| Eleventh layer (First blue-sensitive layer) | | |
| Emulsion A | silver | 0.08 |
| Emulsion B | silver | 0.07 |
| Emulsion F | silver | 0.07 |
| Sensitizing dye VIII | | $3.5 \times 10^{-4}$ |
| EX-9 | | 0.721 |
| EX-8 | | 0.042 |
| HBS-1 | | 0.28 |
| Gelatin | | 1.10 |
| Twelfth layer (Second blue-sensitive emulsion layer) | | |
| Emulsion G | silver | 0.45 |
| Sensitizing dye VIII | | $2.1 \times 10^{-4}$ |
| EX-9 | | 0.154 |
| Ex-10 | | 0.007 |
| HBS-1 | | 0.05 |
| Gelatin | | 0.78 |
| Thirteenth layer (Third blue-sensitive emulsion layer) | | |
| Emulsion H | silver | 0.77 |
| Sensitizing dye VIII | | $2.2 \times 10^{-4}$ |
| EX-9 | | 0.20 |
| HBS-1 | | 0.07 |
| Gelatin | | 0.69 |
| Fourteenth layer (First protective layer) | | |
| Emulsion I | silver | 0.20 |
| U-4 | | 0.11 |
| U-5 | | 0.17 |
| HBS-1 | | 0.05 |
| Gelatin | | 1.00 |
| Fifteenth layer (Second protective layer) | | |
| Poly(methyl methacrylate) particle (diameter: about 1.5 μm) | | 0.54 |
| S-1 | | 0.20 |
| Gelatin | | 1.20 |

In each layer gelatin hardener H-1, gelatin reservative and mildewcide 1,2-benzisothiazoline-3-one, 2-phenoxyethanol, and phenetyl alcohol, and surface-active agent were added in addition to the above components.

| | Average AgI Content (%) | Grain Size Average Diameter (μm) | Grain Size Deviation Coefficient (%) | Ratio of Diameter/ Thickness | Ratio of Silver Amount (AgI content %) |
|---|---|---|---|---|---|
| Emulsion | | | | | |
| A | 4.0 | 0.45 | 27 | 1 | Core/Shell = ½(13/1) Double layer Structure Grains |
| B | 8.9 | 0.70 | 14 | 1 | Core/Shell = 3/7(25/2) Double layer Structure Grains |
| C | 10 | 0.75 | 30 | 2 | Core/Shell = ½(24/3) Double layer Structure Grains |
| D | 16 | 1.05 | 35 | 2 | Core/Shell = 4/6(40/0) Double layer Structure Grains |
| E | 10 | 1.05 | 35 | 3 | Core/Shell = ½(24/3) Double layer Structure Grains |
| F | 4.0 | 0.25 | 28 | 1 | Core/Shell = ½(13/1) Double layer Structure Grains |
| G | 14.0 | 0.75 | 25 | 2 | Core/Shell = ½(40/0) Double layer Structure Grains |
| H | 14.5 | 1.30 | 25 | 3 | Core/Shell = 37/63(34/3) Double layer Structure Grains |
| I | 1 | 0.07 | 15 | 1 | Uniform Grains |

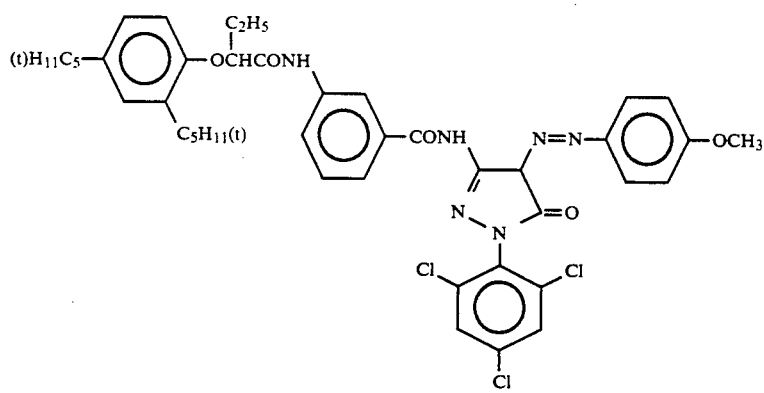
EX-1
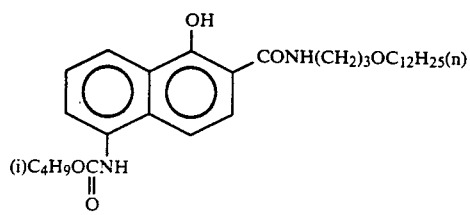
EX-2
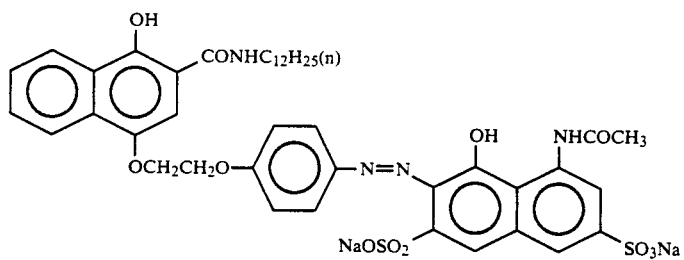
EX-3
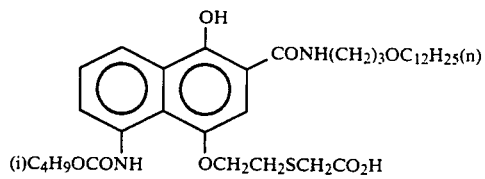
EX-4
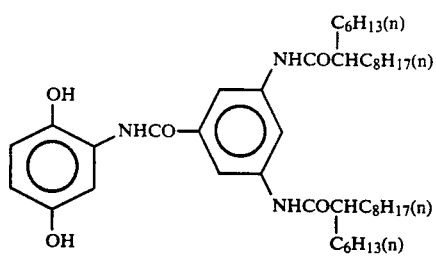
EX-5
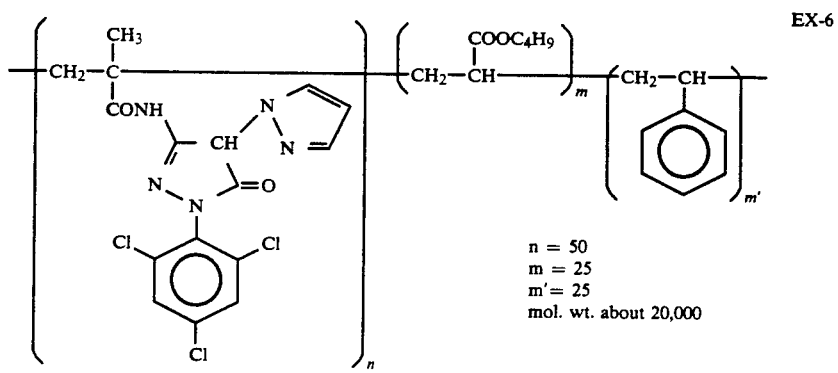
EX-6
n = 50
m = 25
m' = 25
mol. wt. about 20,000

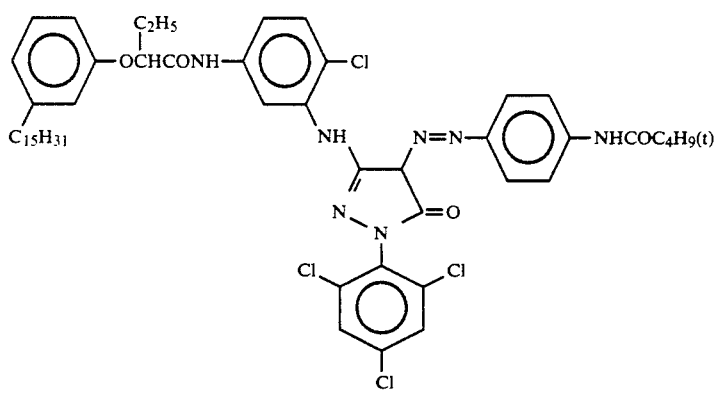
EX-7
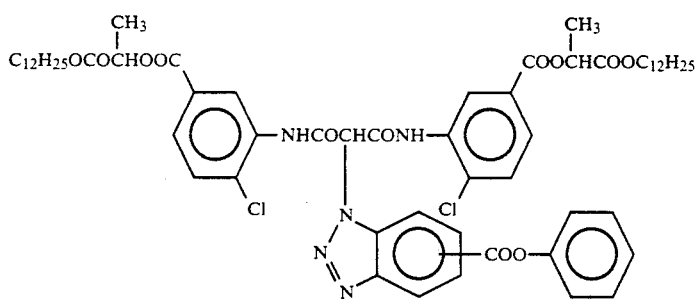
EX-8
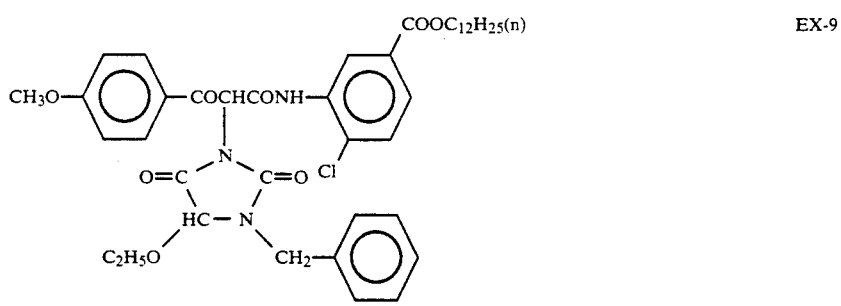
EX-9
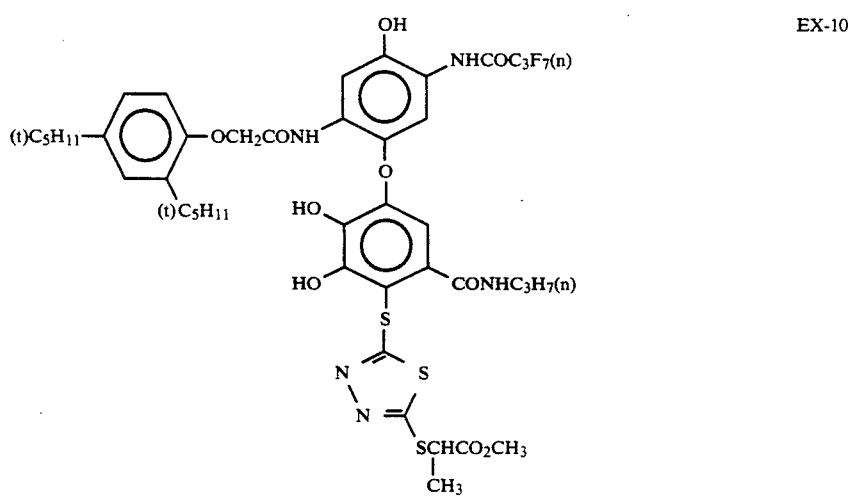
EX-10

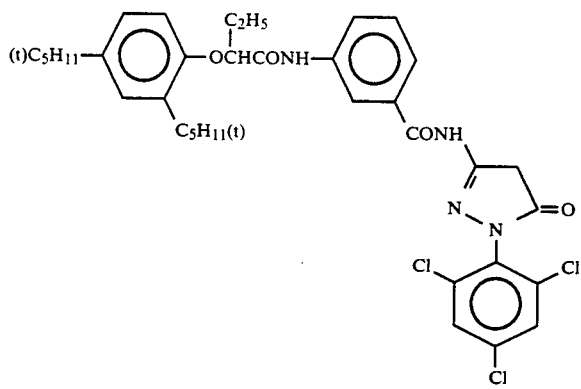
EX-11
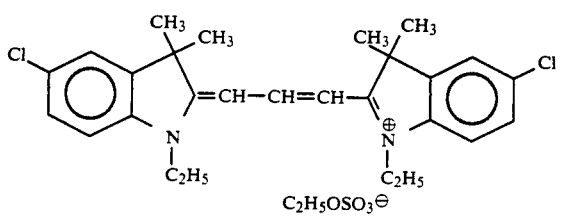
EX-12
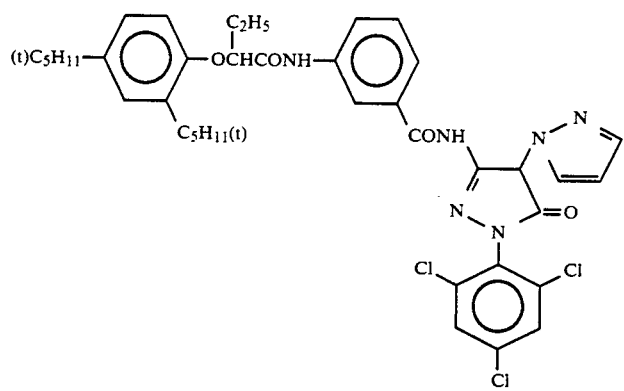
EX-13
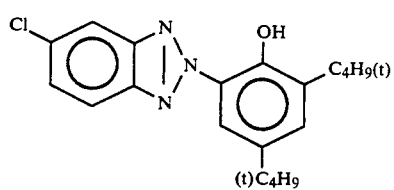
U-1
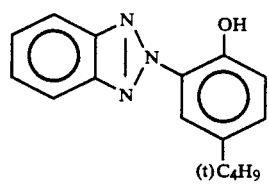
U-2
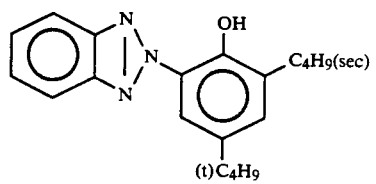
U-3

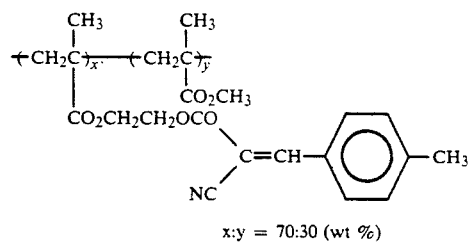
U-4
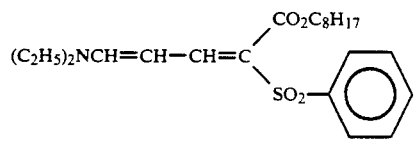
U-5
Tricresyl phosphate   HBS-1
Di-n-butyl phthalate   HBS-2
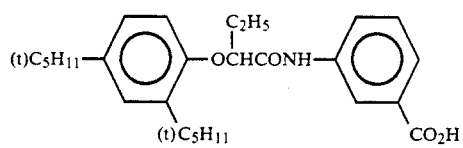
HBS-3
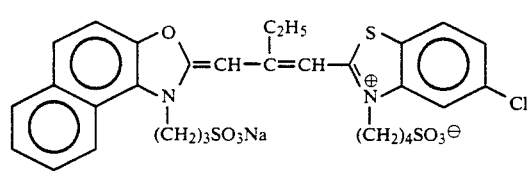
Sensitizing dye I
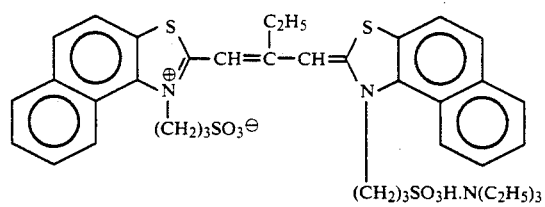
Sensitizing dye II
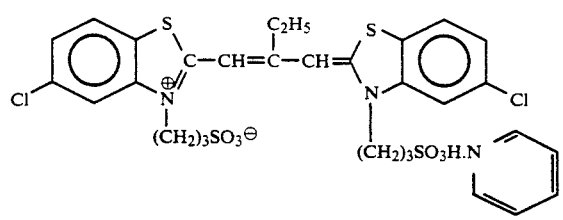
Sensitizing dye III
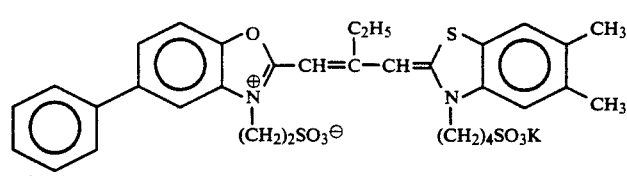
Sensitizing dye V
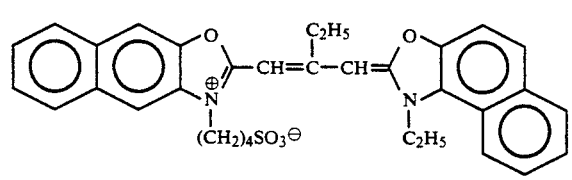
Sensitizing dye VI

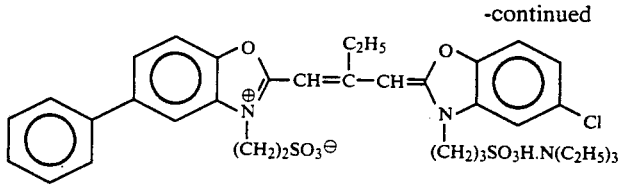

Sensitizing dye VII

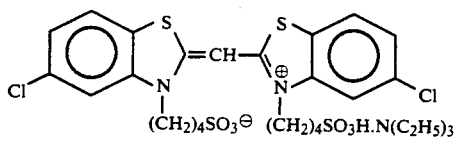

Sensitizing dye VII

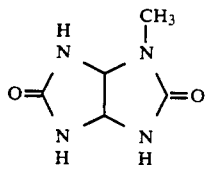

S-1

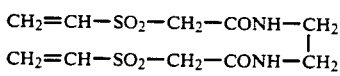

H-1

The thus-prepared photographic material 401 was subjected to an exposure of light and then to a processing process described below in an automatic processor, until the accumulated replenishing amount of color developer reached to three times that of the mother solution tank.

TABLE 5

| Process | Processing process | | | |
|---|---|---|---|---|
| | Time | Temperature | Replenisher* | Tank Volume |
| Color development | 3 min. 15 sec. | 38° C. | 33 ml | 20 l |
| Bleaching | 6 min. 30 sec. | 38° C. | 25 ml | 20 l |
| Water washing | 2 min. 10 sec. | 24° C. | 1200 ml | 20 l |
| Fixing | 4 min. 20 sec. | 38° C. | 25 ml | 20 l |
| Water washing (1) | 1 min. 05 sec. | 24° C. | ** | 10 l |
| Water washing (2) | 1 min. 00 sec. | 24° C. | 1200 ml | 10 l |
| Stabilizing | 1 min. 05 sec. | 38° C. | 25 ml | 10 l |
| Drying | 4 min. 20 sec. | 55° C. | | |

Note:
*Replenisher amount per 1 meter of 35 mm width
**Countercurrent flow mode from the tank of (2) to the tank of (1)

The compositions of each processing solution were as follows:

| | Mother solution (g) | Replenisher (g) |
|---|---|---|
| Color developer | | |
| Diethylenetriaminepentaacetic acid | 1.0 | 1.1 |
| 1-Hydroxyethylidene-1,1-diphophonic acid | 3.0 | 3.2 |
| Sodium sulfite | 4.0 | 4.4 |
| Potassium carbonate | 30.0 | 37.0 |
| Potassium bromide | 1.4 | 0.7 |
| Potassium iodide | 1.5 mg | — |
| Hydroxylamine sulfate | 2.4 | 2.8 |
| 4-(N-ethyl-N-β-hydroxyethylamino)-2-methylaniline sulfate | 4.5 | 5.5 |
| Water to make | 1.0 l | 1.0 l |
| pH | 10.05 | 10.10 |
| Bleaching solution | | |
| Iron (III) sodium ethylenediamine | 100.0 | 120.0 |

| | Mother solution (g) | Replenisher (g) |
|---|---|---|
| tetraacetate trihydrate | | |
| Disodium ethylenediaminetetraacetate | 10.0 | 11.0 |
| Ammonium bromide | 140.0 | 160.0 |
| Ammonium nitrate | 30.0 | 35.0 |
| Aqueous ammonia (27%) | 6.5 ml | 4.0 ml |
| Water to make | 1.0 l | 1.0 l |
| pH | 6.0 | 5.7 |
| Fixing solution | | |
| Disodium ethylenediaminetetraacetate | 0.5 | 0.7 |
| Ammonium sulfite | 7.0 | 8.0 |
| Ammonium bisulfite | 5.0 | 5.5 |
| Ammonium thiosulfite (70%) | 170.0 ml | 200.0 ml |
| Water to make | 1.0 l | 1.0 l |
| pH | 6.7 | 6.6 |
| Stabilizing solution | | |
| Formalin (37%) | 2.0 ml | 3.0 ml |
| Polyoxyethylene-p-monoonylphenyl-ether (average polymerization degree: 10) | 0.3 | 0.45 |
| Disodium ethylenediaminetetraacetate | 0.05 | 0.08 |
| Water to make | 1.0 l | 1.0 l |
| pH | 5.0–8.0 | 5.0–8.0 |

When the same processing as the above, except that the cyan coupler in the red-sensitive layer of Sample 401 was changed to exemplified compound (1) of the present invention, was effected, improved good photographic characteristics were obtained, similar to Examples 1 to 3.

REFERENCE EXPERIMENTAL EXAMPLE

To investigate the basic hue of the cyan dye obtained from a coupler of the present invention, Dye (53) given below was formed from compound (46), obtained using a similar synthesis process, and the absorption spectrum and molecular extinction coefficient were measured.

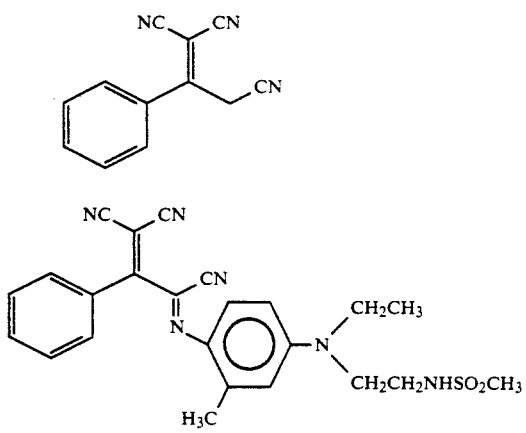

(46)

(53)

Compound (53) was synthesized according to the following scheme.

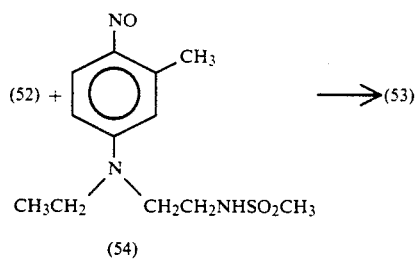

400 mg of (52) and 590 mg of (54) were dissolved in 10 ml of ethanol, and 1 ml of glacial acetic acid was added dropwise. The reaction mixture was stirred for 1 hour at room temperature, and then 50 ml of ethyl acetate and 50 ml of water were added followed by washing with water three times. After the ethyl acetate layer was dried over magnesium sulfate, the ethyl acetate was distilled off under reduced pressure and the residue was purified by column chromatography, to obtain Compound (53).

Molar extinction coefficients in ethyl acetate solution are shown in Table 6, and absorption spectra are shown in FIG. 1.

In FIG. 1, ———represents the absorption spectrum of the dye (53) obtained by the coupling reaction of a compound of the present invention with the oxidized product of a color-developing agent, and ------ represents the absorption spectrum of the dye derived from comparative compound (1).

TABLE 6

| Dye | Molecular Extinction Coefficient[1)] |
|---|---|
| (53) | $4.2 \times 10^4$ |
| Comparative Compound (1) | $2.7 \times 10^4$ |
| Comparative Compound (2) | $2.6 \times 10^4$ |

Note:
[1)]$l \cdot mol^{-1} \cdot cm^{-1}$

Comparative Compound (1)

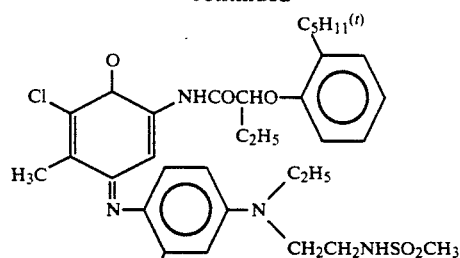

Comparative Compound (2)

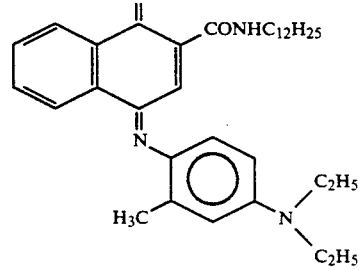

As is apparent from Table 6 and FIG. 1, in comparison with prior known phenols and naphthols, the couplers of the present invention can provide dyes high in molecular extinction coefficient and less in subsidiary absorption.

Having described our invention as related to the embodiment, it is our intention that the invention not be limited by any of the details of the description, unless otherwise specified, but rather be construed broadly within its spirit and scope as set out in the accompanying claims.

What we claimed is:

1. A silver halide color photographic material comprising a cyan coupler represented by the formula (III):

Formula (III)

wherein W represents a hydrogen atom or an atom or group capable of being released when the coupler is subjected to a coupling reaction with the oxidized product of an aromatic primary amine developing agent, $R_4$ and $R_5$ represents a substituent, provided that at least one of $R_4$ and $R_5$ represents an electron-attractive substituent and provided that $R_4$ and $R_5$ do not bond to form a ring.

2. The silver halide color photographic material as claimed in claim 1, wherein the compound represented by formula (III) is present as a cyan coupler in the photosensitive silver halide emulsion layer of the silver halide color photographic material.

3. The silver halide color photographic material as claimed in claim 1, wherein the compound represented by formula (III) is present in a red-sensitive silver halide emulsion layer of the silver halide color photographic material.

4. The silver halide color photographic material as claimed in claim 1, wherein the color coupler represented by formula (III) is contained in an amount of 0.002 to 2 mol per mol of photosensitive silver halide.

5. The silver halide color photographic material as claimed in claim 1, wherein at least one of $R_4$ and $R_5$ in formula (III) represents an electron-attractive substituent having a value of the Hammett substituent constant $\sigma_p$ of 0.10 or over.

6. The silver halide color photographic material as claimed in claim 1, wherein, when $R_4$ or $R_5$ is not an electron-attractive substituent, $R_4$ or $R_5$ is selected from the group consisting of an aliphatic group, an aromatic group, and a heterocyclic group.

7. The silver halide color photographic material as claimed in claim 1, wherein $R_4$ and $R_5$ are selected from the group consisting of an aliphatic group having 1 to 36 carbon atoms, an aromatic group having 6 to 36 carbon atoms, 2-furyl, 2-thienyl, 2-pyrimidyl and 2-thiazolyl.

8. A method for forming a color image, which comprises developing a silver halide color photographic material by a color developer containing an aromatic primary amine derivative, in the presence of the cyan coupler represented by formula (III) in claim 1.

* * * * *